United States Patent [19]
Scherz et al.

[11] Patent Number: 5,955,585
[45] Date of Patent: Sep. 21, 1999

[54] CATALYTIC CONDENSATION METHOD FOR THE PREPARATION OF CHLOROPHYLL AND BACTERIOCHLOROPHYLL DERIVATIVES

[75] Inventors: Avigdor Scherz; Yoram Salomon, both of Rehovot, Israel; Leszek Fiedor, Cieszyn, Poland

[73] Assignee: Yeda Research and Development Co., Ltd., Rehovot, Israel

[21] Appl. No.: 08/461,243

[22] Filed: Jun. 5, 1995

Related U.S. Application Data

[62] Division of application No. 08/097,384, Jul. 26, 1993, Pat. No. 5,726,169.

[30] Foreign Application Priority Data

Jul. 26, 1992 [IL] Israel ........................................ 102645

[51] Int. Cl.⁶ .................................................... C07K 17/06
[52] U.S. Cl. ......................... 530/408; 530/344; 530/399; 530/409; 530/410; 435/68.1; 435/117; 435/119; 435/193
[58] Field of Search ...................................... 435/193, 117, 435/68.1, 119; 530/344, 345, 399, 408, 409, 410

[56] References Cited

U.S. PATENT DOCUMENTS 4,876,190  10/1989  Rectenwald .
5,567,687  10/1996  Magda et al. ............................ 514/44

OTHER PUBLICATIONS

Boxer et al., "Chlorophyl–Amino Acid Interactions in Synthetic Models" (1981) v. 21 N. 4, pp. 259–264.

Zubay, "Biochemistry" (1993) pp. 64–66.

Biotech Abs 88–11013 Michalski et al JA Chem Soc. (1988) 110; 17, 5881–91.

*Primary Examiner*—Cecilia J. Tsang
*Assistant Examiner*—Patrick R. Delaney
*Attorney, Agent, or Firm*—Helfgott & Karas, P.C.

[57] ABSTRACT

Conjugates of chlorophyll (Chl) and bacteriochlorophyll (Bchl) derivatives with amino acids, peptides and proteins are provided by the invention. The amino acid, peptide or protein residue is linked to the 17-propionic acid group of a Chl or Bchl residue directly or through a chain. The conjugates are for use as photosensitizers in photodynamic therapy and in diagnostics of tumors. Conjugation with cell-specific ligands, such as hormones, growth factors or tumor-specific antibodies, will target the Chl or Bchl moiety to the tumor site. Thus, conjugates with melanocyte stimulating hormones are suitable for photodynamic therapy of melanoma tumors.

19 Claims, 18 Drawing Sheets

Haematoporphyrin (Hp)

$R_1 = R_2 = CH(OH)CH_3$ a) Struture of Chlorophyll a and the IUPAC numbering system b) Structure of Bacteriochlorophyll a

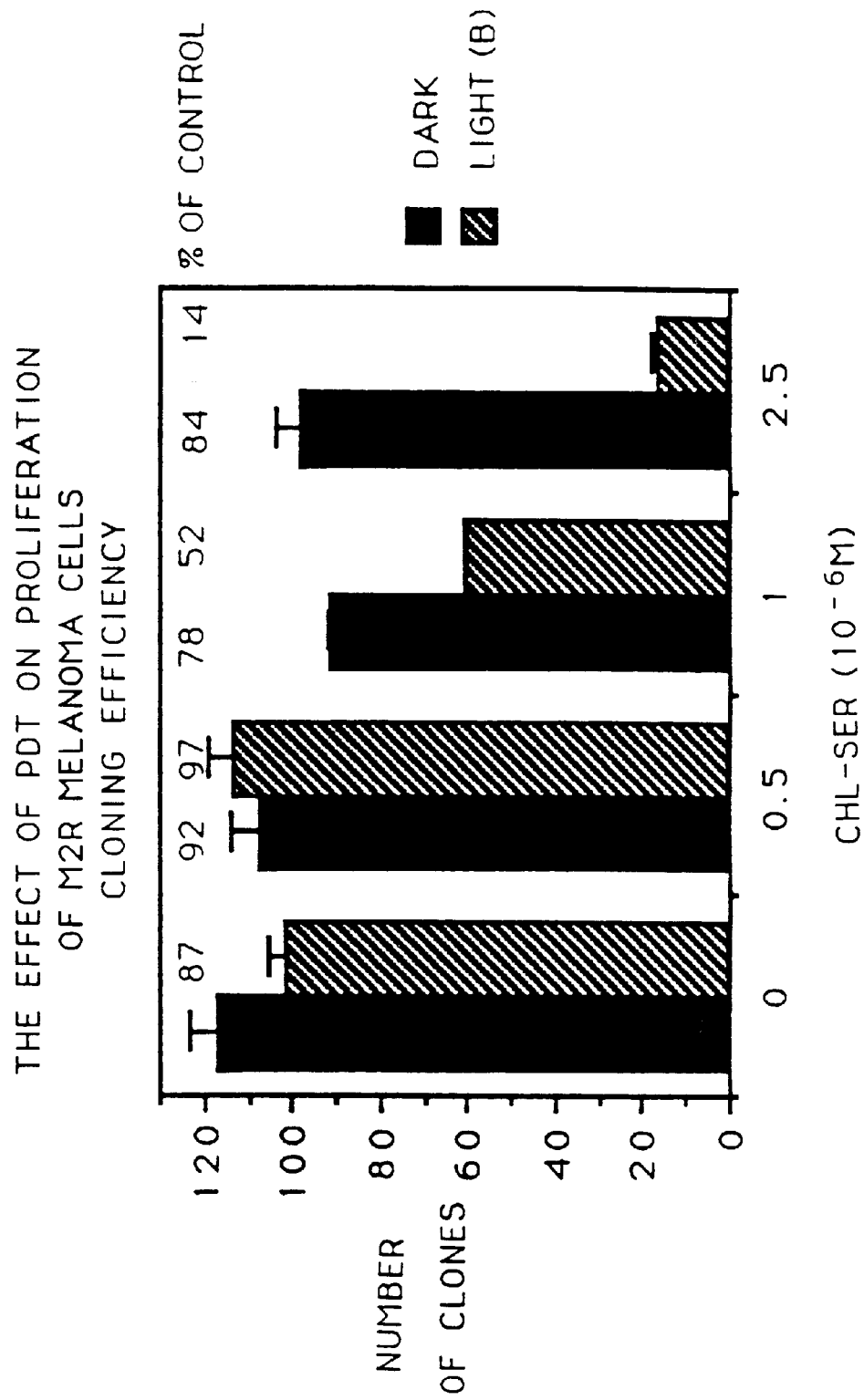

  
FIG.18A　　　FIG.18B　　　FIG.18C
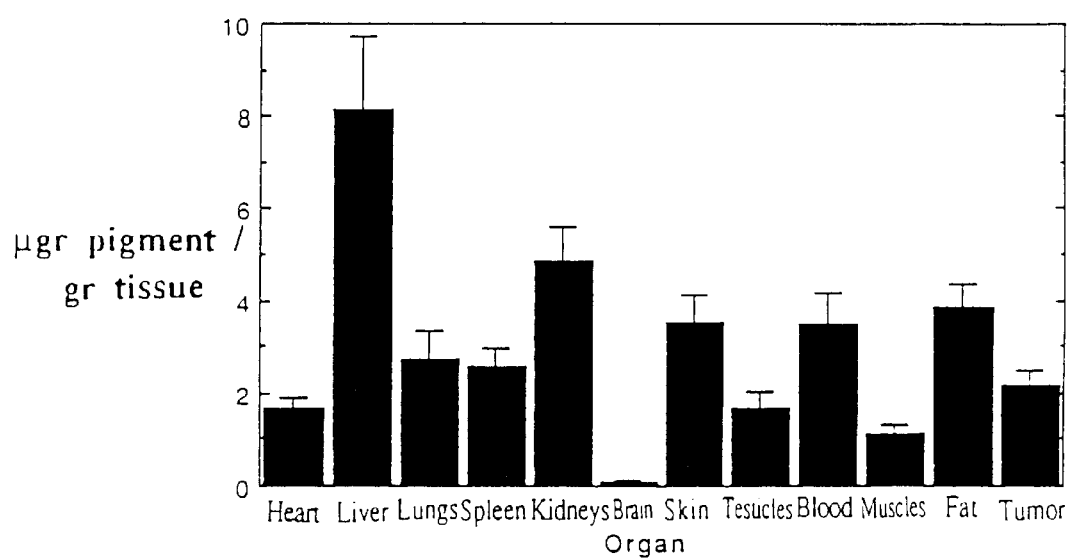
FIG.19

CATALYTIC CONDENSATION METHOD FOR THE PREPARATION OF CHLOROPHYLL AND BACTERIOCHLOROPHYLL DERIVATIVES

This is a division of application Ser. No. 08/097,384, filed Jul. 26, 1993 now U.S. Pat. No. 5,726,169.

FIELD OF THE INVENTION

The present invention relates to novel derivatives of chlorophyll (Chl) and of bacteriochlorophyll (Bchl), to their preparation and their application in photodynamic therapy, as well as in fluorescence detection and monitoring techniques.

BACKGROUND OF THE INVENTION

During the last two decades, there has been an increasing interest in the utilization of photosensitizers for cancer therapy. In this technique, known as photodynamic therapy (PDT), singlet oxygen, oxygen radicals and superoxides or peroxides are produced by in situ photosensitization of previously applied chromophores and intoxicate the malignant cells (Dougherty, 1987). The technique utilizes non-toxic drugs in combination with non-hazardous photosensitizing irradiation, and has the potential of being more selective yet no less destructive when compared with the commonly used chemotherapy or radiotherapy, and therefore it is expected to increase the quality of life of the treated patients.

The photosensitizers used in PDT need to have a high quantum yield for singlet oxygen production and high affinity and selectivity to the malignant tissue. Porphyrins have a relatively high quantum yield for the formation of an excited triplet state and the difference between the energies of this state and their singlet ground state makes them good energy donors to excite the ground state (triplet) oxygen to its singlet state. It has been known for some time that hematoporphyrin (HP) (FIG. 1) and hematoporphyrin derivative (HPD) tend to accumulate in neoplastic tissues. Thus, HP and HPD mixtures have become the preferred compounds for PDT.

The commercially used HPD mixture as photodynamic agent, Photofrin II (Quarda Logic Technologies, Inc., Vancouver, BC, Canada) contains a high proportion of ether-linked HP oligomers that have high extinction coefficient values around 400 nm (the so-called Soret band), but much smaller values in the visible (500–630 nm; the so-called Q bands). Unfortunately, due to the extensive attenuation of UV-Visible light by the animal tissue, the quantum yield of photosensitization by HPD in situ is very low. Therefore, intensive illumination and large amounts of HPD are required for efficient treatment of tumors. As the amount of applied HPD increases, the chances of its accumulation in normal tissues and the accompanying risk of damaging non-malignant sites, profoundly increases. An additional disadvantage of HPD related analogues is their slow clearance from the human body. Patients treated with HPD suffer from skin phototoxicity over periods of weeks.

The strong attenuation of UV-VIS light by the animal tissue and the limited specificity of HPD to the malignant sites have motivated research and synthesis of new photo-therapeutic agents that absorb light beyond 650 nm and have increased retention in the malignant site (McRobert et al., 1989).

In order to increase the retention in, and the specificity to, malignant tissues, various porphyrin derivatives containing particular chemical groups attached to the pyrrole residues of the porphyrin structure have been tested. The red shift of the compounds absorption relative to HPD is achieved by variations in the porphyrin $\pi$-electron system.

Following this approach, there has been an increasing interest in using Chl and Bchl derivatives as PDT agents (Kreimer-Birnbaum, 1989; Spike and Bommer, 1991). Chls and Bchls are di- and tetrahydroporphyrin derivatives, respectively, consisting of 4 pyrrole and one isocyclic rings linked to each other and to the atom of Mg, as depicted in FIG. 2 for chlorophyll a (Chla) and in FIG. 3 for bacteriochlorophyll a (Bchla), M representing Mg and the radical R being phytyl or geranylgeranyl in Bchla, and phytyl in Chla. The Bchla molecule differs from the Chla molecule by having two more $\beta$-carbon (peripheral carbons of the pyrrole rings) reduced. The variety of Chls and Bchls results from the variation of substituents at the macrocycle or the alcohol residue that esterifies the 17-propionic acid residue. In the naturally occurring Bchla, the alcohol residue is phytyl or geranylgeranyl, while in Bchlb, for example, it is geranylgeranyl. The acids derived from chlorophyll and bacteriochlorophyll are designated chlorophyllide (Chlide) and bacteriochlorophyllide (Bchlide), respectively. The free acids derived from Chla and Bchla are designated Chlidea and Bchlidea, respectively. The compounds derived from Chl and Bchl devoid of a central metal atom are designated pheophytin (Pheo) and bacteriopheophytin (Bpheo), respectively. The pheophytins derived from Chla and Bchla are designated Pheoa and Bpheoa, respectively. The free acids derived from pheophytin and bacteriopheophytin are designated pheophorbide and bacteriopheophorbide, respectively.

The Chls and the Bchls harvest solar energy and initiate electron transfer in biological photosynthesis. Their lowest-energy transitions (the so-called $Q_y$ transitions) in the monomeric forms are found at 670–800 nm and can be shifted up to 1000 nm in aggregated forms. These transitions have extremely high extinction coefficients. The probability of inter-system crossing from the excited singlet state of the Chls and Bchls to their lowest triplet state is fairly high (30–50%) and assures a high yield of excited oxygen molecules. In fact, the photosensitization of oxygen by Chls and Bchls is underlined by the fact that they are involved in important degradative processes in photosynthetic bacteria and plants and therefore all photosynthetic organisms have a variety of protective mechanisms against singlet oxygen or oxygen radicals. Since Chls and Bchls are natural compounds that are ordinarily consumed by animals, their in vivo degradation is very fast relative to HP or HPD (Llewellyn, et al. 1990). This is an important advantage that reduces the patient subjection to prolonged irradiation.

Yet, there are several problems in using the native Chl or Bchl extracts for PDT. First, they are hard to deliver to the malignant site because they are strongly hydrophobic. Second, they are very labile under normal delivery conditions, i.e., in the presence of oxygen at room temperature and under normal light conditions. Third, they have no moiety to target them specifically to the malignant tissue. Due to these limitations, the potential of these photosynthetic pigments as sensitizers in PDT is presently hard to realize. It would be highly desirable to synthesize Chl and Bchl derivatives that would overcome these difficulties and could be successfully used in PDT. It is the object of the present invention to provide such derivatives.

SUMMARY OF THE INVENTION

The side groups of Chl and Bchl determine the molecule's overall affinity to different environments.

It has now been found according to the present invention that new Chl and Bchl derivatives can be prepared for use as photosensitizers in therapy and diagnostics by modification of the ester group at the C17-propionic acid side group of the Chl or Bchl structure.

The present invention thus relates to new Chl and Bchl derivatives of the general formula I

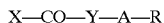

in which
x—CO— represents a C17-propionyl Chl or Bchl residue; Y is O, S or NH; A is a covalent bond or a straight or branched, saturated or unsaturated hydrocarbon chain having from 2 to 20 carbon atoms and which may be substituted and/or interrupted by functional groups, heteroatoms and/or carbocyclic or heterocyclic moieties, and R is an amino acid, a peptide or a protein residue or a derivative thereof.

The term "Chl or Bchl residue" herein means any derivative of Chl or Bchl, both natural and synthetic derivatives, and includes the compounds in which the central Mg atom has been deleted or substituted by other divalent metals, such as Zn, V, Cu, Co, Ni or Sn. Bchl derivatives are preferred according to the invention.

In a preferred embodiment, Y is O and X—CO— is the residue of Chla or Bchla, shown in FIGS. 2 and 3, respectively.

The hydrocarbon chain A has preferably from 5 to 20 carbon atoms. It may be saturated or unsaturated, interrupted by heteroatoms, such as O, N and/or S, and/or substituted or interrupted by mono- or poly- carbocyclic or heterocyclic moieties, and/or functional groups, such as OH, $NH_2$, $CONH_2$, COOH, etc. For example, A may comprise or be the residue of a carbohydrate, e.g., of a mono- or oligosaccharide, of a triglyceride or other lipidic moieties, of a polycarbocyclic ring, e.g., steroids, such as cholesterol, or of a heterocyclic compound, e.g., uracyl and 2,5-dioxo-3,6-dihydroxymethylpiperazine and uracyl A will be linked to R through a functional group, e.g., ester, amide, ether, etc.

The radical R may be derived from an amino acid or a derivative thereof, such as serine, tyrosine and lysine and derivatives thereof, e.g., L-serine or tyrosine methyl esters, or from a peptide, e.g., seryl serine methyl ester, melanocyte stimulating hormones (MSH), or from a protein.

In particular it is envisaged by the invention the conjugation of Chl and Bchl with different amino acids, and further conjugation of these Chl/Bchl amino acid conjugates with hormones, growth factors or derivatives thereof, or tumor-specific antibodies, or any other cell specific ligands, thus obtaining suitable site-directed photosensitizers (SPD). An example of a peptidic hormone used in the invention is one of the melanocyte-stimulating hormones (MSH) (melanotropins), such as α-, β- or gamma-MSH, that specifically bind to receptors in the melanocytes, and can thus target the photosensitizing moiety into melanoma tumors.

The invention further comprises processes for the preparation of the compounds of formula (I).

Also included in the invention are compositions comprising a compound of formula (I) for diagnostic and photodynamic therapy purposes, and a method of photodynamic therapy of cancer patients which comprises treatment of the patient with a compound of formula (I) followed by local irradiation.

DESCRIPTION OF THE DRAWINGS

FIG. 13 shows the effect of PDT on proliferation of M2R melanoma cells cloning efficiency upon treatment with Chla-L-Ser-OMe with (light) and without (dark) subsequent irradiation.

FIGS. 18 A–C show magnetic resonance imaging (MRI) of M2R melanoma tumor (T) implanted in a CD1 nude mouse treated with Bchla-L-Ser-OMe, before (A), two weeks after the first treatment (B), and two weeks after a second treatment (C). Whereas some recurrence (R) is seen in (B), there is no recurrence in (C).

FIG. 19 shows the distribution of Chla-L-Ser-OMe in several organs of CD1 nude mice 12 hours after treatment.

DETAILED DESCRIPTION OF THE INVENTION

The present invention provides conjugates of Chl and Bchl with amino acids, peptides and polypeptides. Of particular importance are conjugates obtained by (a) conjugation of Chl and Bchl with different amino acids and derivatives thereof; (b) further conjugation of Chl- and Bchl-amino acid conjugates with hormones, e.g., α-melanotropin, or (c) with tumor specific antibodies, and (d) substitution of the central Mg in the Chl and Bchl conjugates with metals that improve the yield of triplet state.

Figure 1:
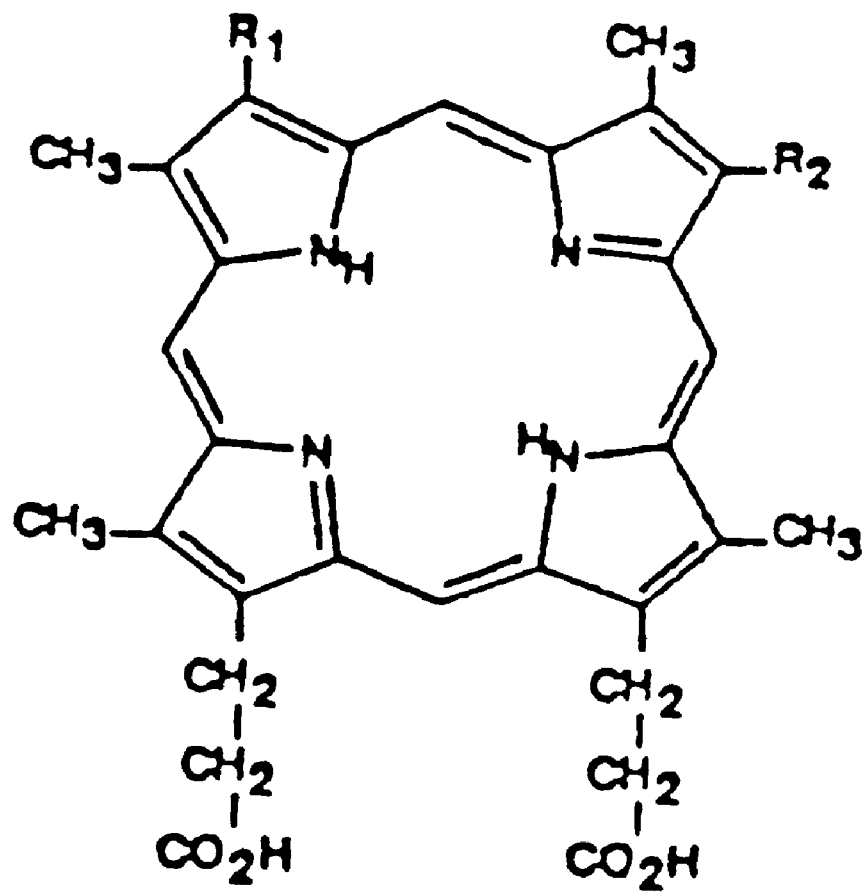
FIG. 1 depicts the structure of hematoporphyrin, HP: R1=R2=—CHOH—$CH_3$.
Figure 2:
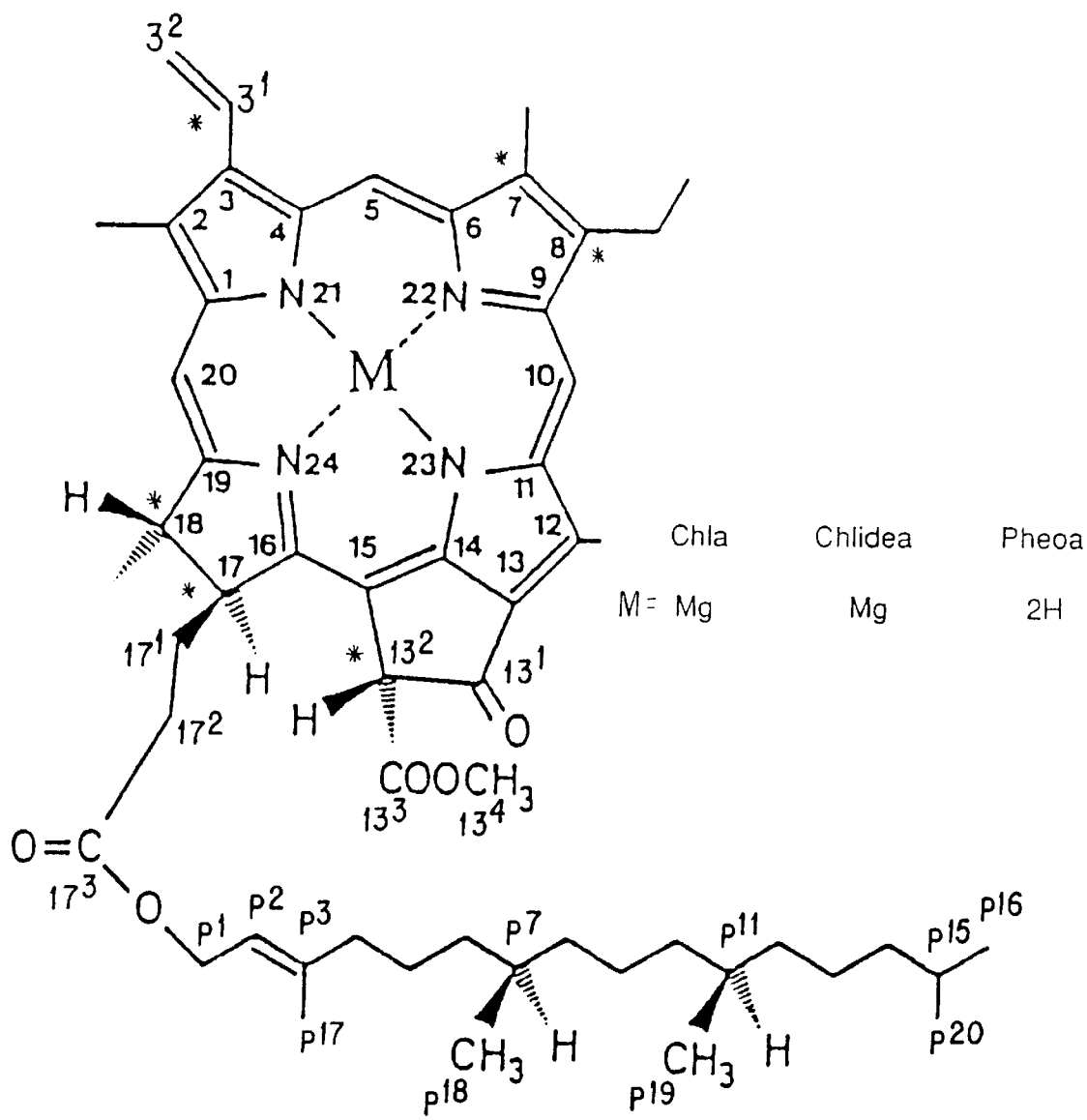
FIG. 2 depicts the structure of Chla (M=Mg, R=phytyl), Chlidea (M—Mg, R=H) and Pheoa (M=2H, R=phytyl).
Figure 3:
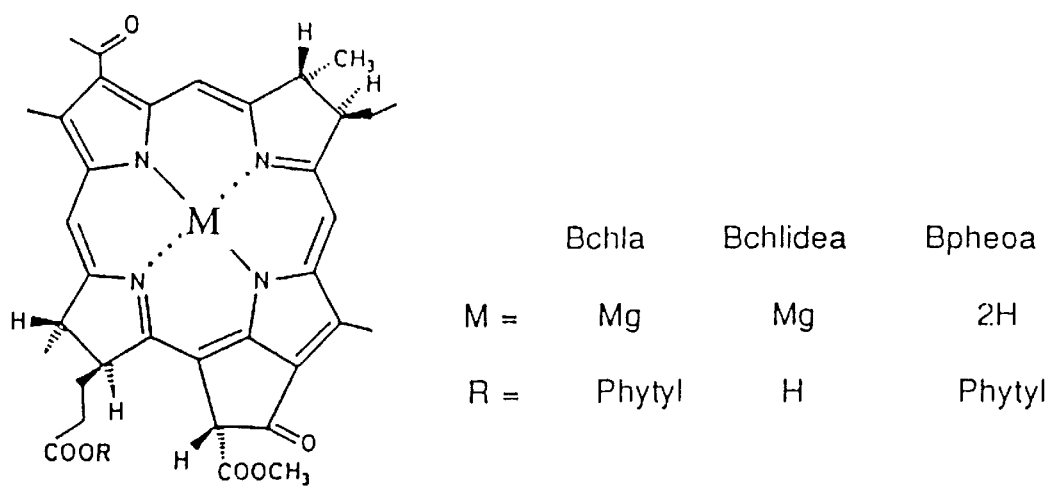
FIG. 3 depicts the structure of Bchla (M=Mg, R=phytyl), Bchlidea (M=Mg, R=H) and Bpheoa (M=2H, R=phytyl).
Figure 4:
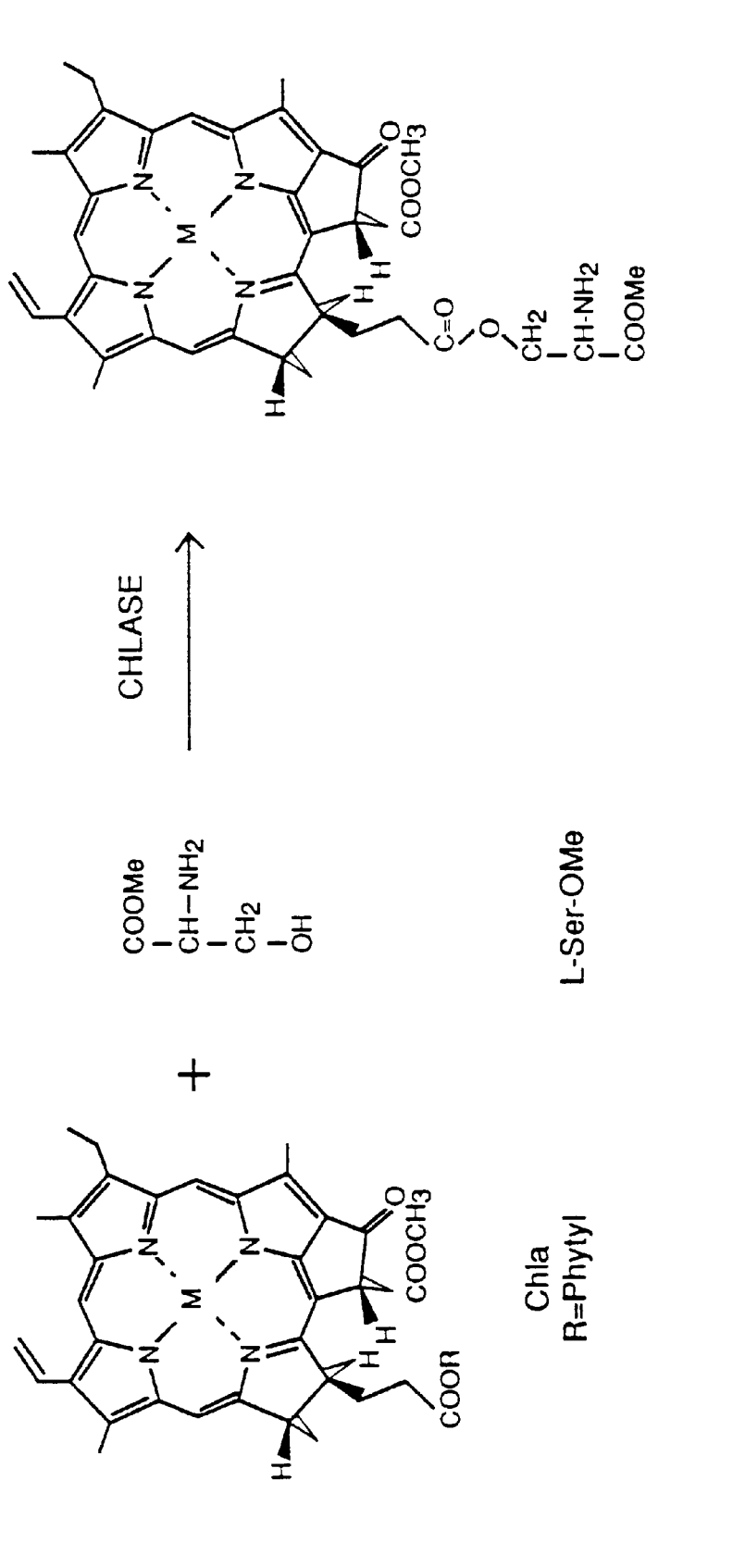
FIG. 4 depicts a scheme of the enzymatic transesterification of Chla with L-serine methyl ester (L-Ser-OMe) in the presence of chlorophyllase (Chlase).

In a preferred embodiment A is a covalent bond, Y is O and the residue R is attached directly to the C17-propionic acid group of Chl or Bchl through an ester bond. These compounds may be prepared by one of two methods:

(1) A novel process of enzymatic transesterification shown in FIG. 4 with the enzyme chlorophyllase (Chlase), extracted with acetone from chloroplasts of plants and stored as acetone powder. The esterification is carried out by incubating chlorophyllase acetone powder with a primary alcohol R—OH, e.g., L-serine methyl ester, in a buffer solution containing detergent, at 37° C. for 1h, adding a Bchl or Chl derivative, e.g. Bchla or Chla, to the resulting suspension and further incubating at 37° C. After removal of the solid acetone powder, the desired ester is extracted from the reaction mixture and purified.

Figure 5:
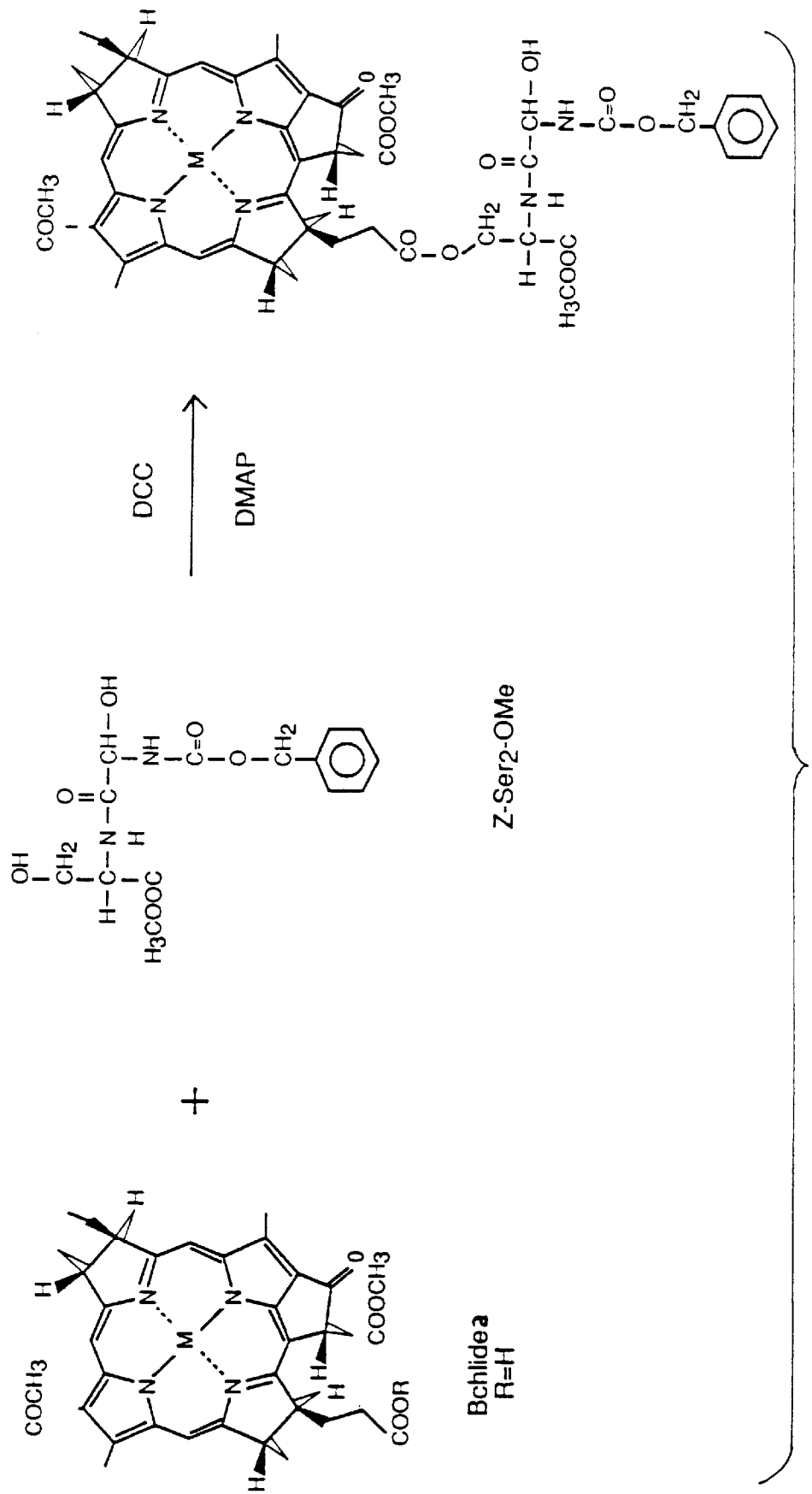
FIG. 5 depicts a scheme for catalytic esterification of Bchlidea with carbobenzoxyserylserine methyl ester (Z-$Ser_2$-OMe, wherein Z is carbobenzoxy).
Figure 6A:
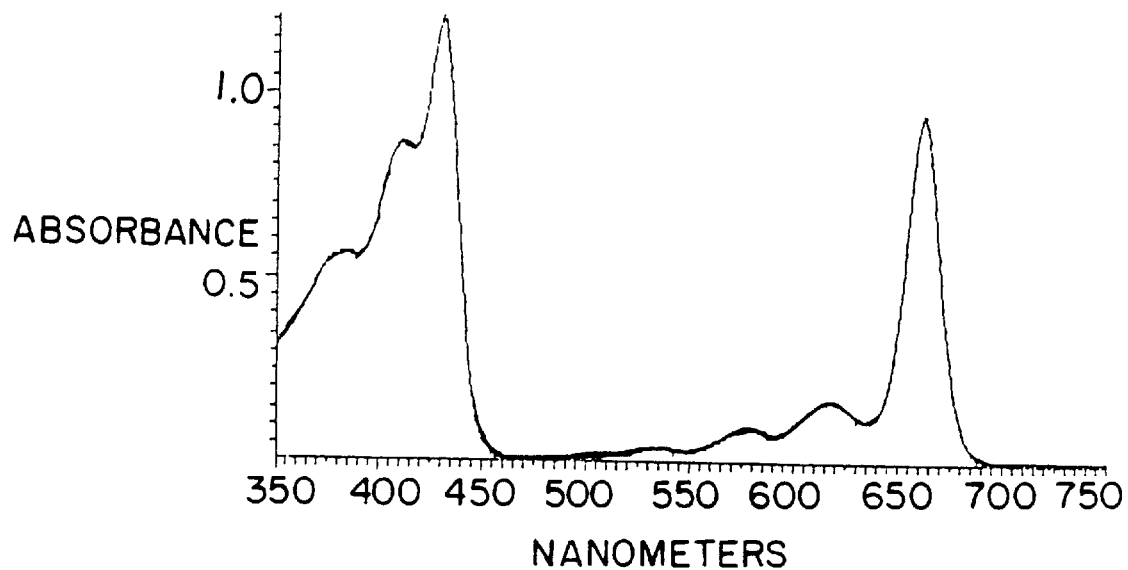
FIG. 6 shows optical absorption spectra of (a)Chla, (b)Chla-L-Ser-OMe, (c)Bchla, and (d)Bchla-L-Ser-OMe, in 100% acetone.
Figure 6B:
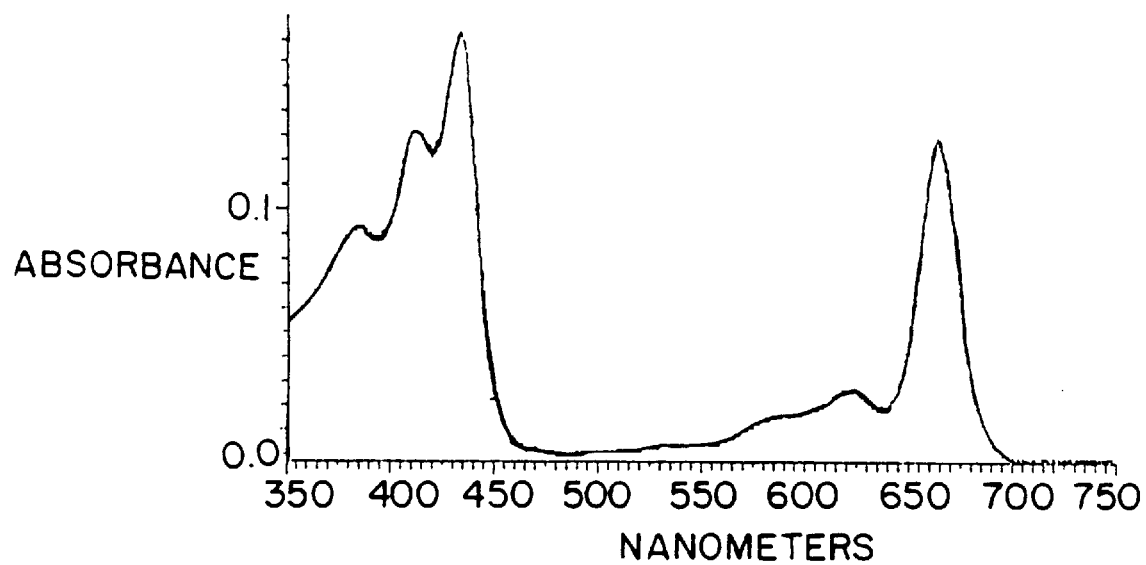
Figure 6C:
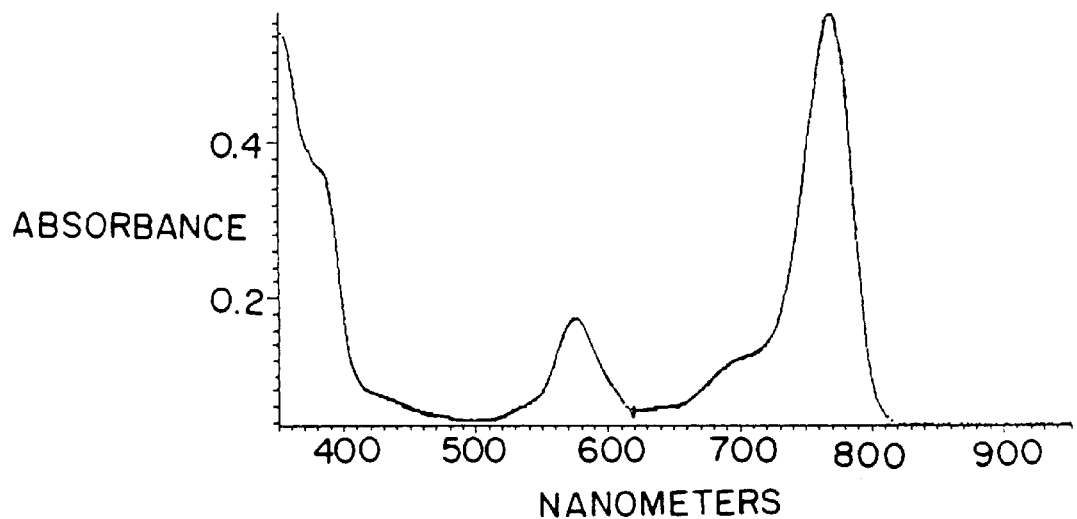
Figure 6D:
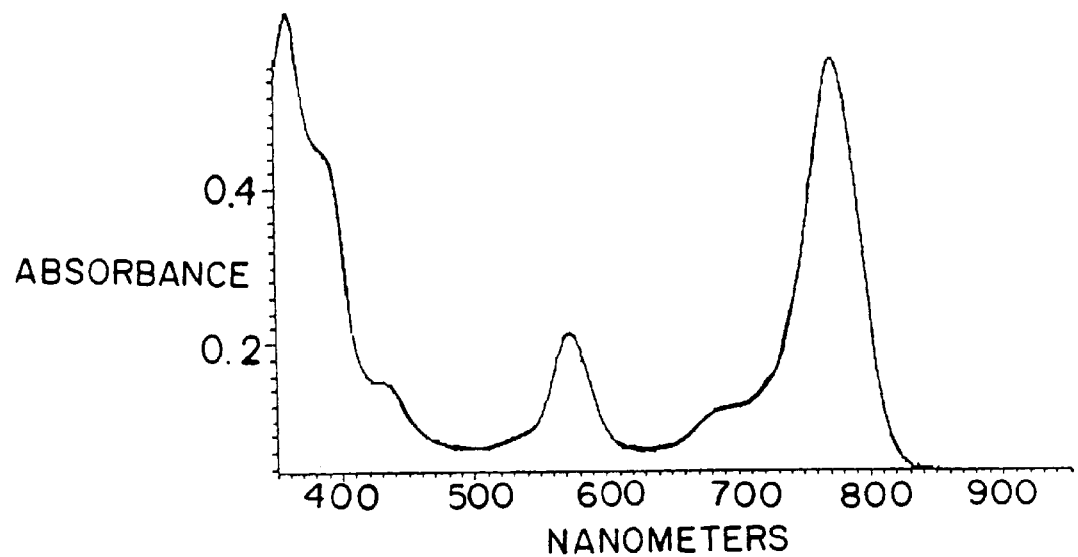

(2) A novel procedure for catalytic condensation of a Chlide or Bchlide derivative, e.g. Chlidea or Bchlidea, with a compound R—OH, e.g., Z-Ser$_2$-OMe, using N-hydroxysuccinimide (NHS) and dicyclohexylcarbodiimide (DCC) or 4-dimethylaminopyridine (DMAP) and DCC to activate the Chlide or Bchlide carboxylic group (FIG. 5). The latter procedure can be used in which pheophorbides and bacteriopheophorbides, the Mg-free analogs of Chlidea and Bchlidea, respectively, are activated prior to condensation with ethylene glycol (Wasielewski, 1980).

Several esters were prepared by the above methods with serine or derivatives thereof, such as L-serine methyl ester hydrochloride, N-trityl-L-serine methyl ester, carbobenzoxyseryl-L-serine methyl ester. These derivatives can be used themselves in the applications of the invention, or they can serve as a bridge to link other suitable molecules to the Chl or Bchl macrocycle.

When an ester is desired and the desired peptide or protein is devoid of an hydroxyl-containing amino acid residue, the Chl or Bchl macrocycle may first be linked to a serine or any other hydroxyl-containing amino acid, or with a derivative thereof, by transesterification of the native compounds or by esterification of the corresponding free acids (Chlide or Bchlide), and the peptide or protein is then linked to the macrocycle through this amino acid residue.

Conjugates of formula I wherein Y is S and A is a covalent bond may be obtained either by enzymatic transesterification of a Chl or Bchl derivative with chlorophyllase and a compound R—SH, e.g, cysteine or a derivative thereof or a cysteine-containing peptide or protein, or by catalytic condensation of a Chlide or Bchlide derivative with a compound R—SH, in the presence of DCC and DMAP.

Conjugates of formula I wherein Y is NH and A is a covalent bond may be obtained by catalytic condensation of a Chlide or Bchlide derivative with a compound R—NH$_2$, e.g. an amine or the terminal amino group of a peptide or protein, in the presence of DCC and DMAP or via NHS and DCC.

When a Chlide or Bchlide derivative is reacted with a peptide or protein comprising amino acid moieties containing hydroxyl, mercapto and/or amino radicals, it may not always be clear whether the conjugation will be through an O or S atom or an NH group, but all such conjugates are encompassed by the present invention, independent of the identification of their structure.

For preparation of metallo-substituted Chl and Bchl derivatives, the Mg is substituted prior to conjugation of the pigment to the amino acid or cell specific ligand. The substitution of the central Mg in Chl and its derivatives with Cu, Ni, Zn, V, Co and other divalent metals is carried out by standard procedures, e.g., treating the corresponding pheophytin with a salt of the desired metal, e.g. Zn acetate or Cu acetate in absolute ethanol at ambient temperature (Hambright, 1975; Hynninen, 1991). In the case of Bchl and its derivatives, the central Mg can be substituted by Zn or Cu by a similar procedure involving treatment with Zn or Cu acetate in glacial acetic acid under argon at elevated temperatures (Fiedor et al., 1993).

When A is a hydrocarbon chain as defined, it will contain an end functional group through which it is attached to the R residue. For example, an ester group is formed by reaction of either the terminal carboxyl group of A with an hydroxyl group of the amino acid or of the terminal hydroxyl group of A with a carboxyl group of the amino acid; an amide group is formed by reaction of the terminal carboxyl group of A with an amino group of the amino acid or of the terminal amino group of A with a carboxyl group of the amino acid, etc.

The new esters have the same optical absorption and photophysical characteristics as the respective Chls and Bchls. Therefore, once residing within the treated tissue, the new Chl and Bchl esters are expected to be efficient photodynamic agents.

The conjugation of proteins, e.g., hormones, growth factors or their derivatives and antibodies, and of cell nutrients, e.g. tyrosine, to the Chl or Bchl moiety is meant to increase their retention in tumor and treated sites. Increasing the red shift allows for a greater depth of penetration while keeping the ubiquity of the natural system. Replacement of the Mg by other metals is meant to optimize the intrinsic and metabolic stability of the Chl or Bchl moiety and its inter-system crossing to the excited triplet state, and also opens the possibility for new diagnostic procedures.

Tumor-specific antibodies will exclusively target the Chl and Bchl moieties to the tumor or treated site, while hormones and cell nutrients may also be taken up by the normal non-transformed transformed counterparts. However, the cells selected as targets to hormones and cell nutrients, such as melanocytes, are scattered among other cells under normal conditions and when transformed into malignant cells, cluster into solid tumors. As a result, the concentration of the photosensitizer in the malignant tissue is expected to increase dramatically relative to its concentration in the normal tissue, where cells are more dispersed, assuring amplification of the PDT effect in the tumor site. This enables effective use of light doses, lower than the damaging threshold of the normal tissue, thus reducing the need for spatially well-defined irradiation. In addition, having very strong fluorescence, the site-directed Chl or Bchl can be used for fluorescence labeling of the tumor site(s) or other targets.

Melanoma tumors are suitable for treatment with the new Chl and Bchl photosensitizers of the invention for several reasons: (a) at early stages (non-metastatic), malignant melanoma and other skin tumors are very accessible to PDT; (b) photodynamic therapy using green light as well as conventional chemotherapy and radiotherapy have failed so far in melanoma treatment; (c) there exist, however, several melanoma specific ligands that can target the photosensitizing moiety into the tumor site, and (d) the use of the long wavelength excitable Chl and Bchl moieties is expected to overcome the shortcomings of the conventional photosensitizers, which due to melanin absorption are screened.

Melanoma tumors evolve from carcinogenic transformation (including UV-induced mutagenesis) of melanocytes. Normal melanocytes comprise a few percent of the normal human skin cell population and are normally found in the basal cell layer between the epidermis and the dermis where each of them is surrounded by 30–40 keratinocytes and one Langerhans cell. PDT faces particular difficult challenge with melanoma tumors since the melanoma tumor cells may contain the insoluble black eumelanins (poly-5,6-indole quinones), which have a broad absorption band around 540 nm and therefore compete with any photosensitizer for the radiation at wavelengths shorter than 650 nm. In addition, the melanin molecules can quench those oxygen radicals that have been formed and thereby prevent the intoxication of vital cell organelles. Consequently, PDT of melanotic melanomas with the commonly used HPD is not very promising. However, having their maximum optical absorption at wavelength above 650 nm, excited Chls and Bchls and their synthetic derivatives should not be shaded by the melanin. Furthermore, melanoma tumor cells (i.e. transformed melanocytes) consume considerable amounts of tyrosine during the synthesis of melanin, have high affinity to melanotropins (the pituitary α-, β- and gamma-melanocyte stimulating hormones (MSH)) and to several known antibodies. Therefore, they can be a good target to tyrosine-, melanocortin-, or antibody-conjugates of Chl and Bchl, provided that the conjugation does not strongly affect ligand recognition by the cell receptors. Since the concentration of the melanocytes increases by a factor of nearly 40 in the melanoma sites (relative to a normal skin tissue), the photodynamic effect is expected to increase drastically.

The present invention thus provides pharmaceutical compositions comprising a Chl or Bchl derivative of the invention for photodynamic therapy of several types of cancer, including brain, ovarian, breast and tumors and skin, lung, esophagus and bladder cancers and other hormone-sensitive tumors.

In one embodiment, the invention relates to photodynamic treatment of malignant melanoma. The photodynamic effect of the compounds is monitored on melanoma cells in tumors and cell cultures. Examples of derivatives that can be used for this purpose are conjugates of Chl or Bchl with α-melanotropin, linked to the pigment moiety either via its serine, tyrosine or lysine residues or through the terminal amino group.

The pharmaceutical compositions of the invention will be administered to the patient by standard procedures used in PDT. The amount of compound to be administered and the route of administration will be determined according to the kind of tumor, stage of the disease, age and health conditions of the patient, but will be much lower than currently used dosage of Photofrin II of about 20–40 mg HPD/kg body weight. The preferable routes of administration are intravenous or direct injection into the solid tumor of the aqueous solution of the active compound comprising conventional pharmaceutically acceptable carriers and additives, and topical treatment of skin tumors with suitable topical compositions.

The invention further relates to a method of photodynamic therapy of cancer which comprises administering to a patient afflicted with a solid tumor cancer a pharmaceutical composition comprising a Chl or Bchl derivative according to the invention, and then irradiating the tumor site with strong light sources at 670–780 nm.

Several applications are thus foreseen for the Chl and Bchl derivatives of the invention, such as for photodestruction of benign or malignant cells or tissue by site-directed photodynamic therapy (SDP). The conjugate carries the Chl or the Bchl molecule to the cells that cluster in tumor tissues upon transformation, but are well separated from each other in normal tissues (e.g. melanocytes in melanoma). As a result, the photodynamic effect of the photosensitizer in the tumor can be higher by orders of magnitude than its effect in the normal tissue. Consequently the threshold of illumination that is destructive for the tumor is expected to be reduced to a level that is non-destructive for the normal tissue. Under these circumstances, the phototoxic effect will be limited to the tumor site even under non-specific irradiation. This application is of a particular importance for tumors that are inaccessible to conventional surgery.

Photodynamic therapy using biphotonic processes (Leupold and Freyer, 1992) is another way to extend the range of sensitization to the near-IR. The high inter-system crossing rate of the Chl and Bchl derivatives and their long wavelength for maximum absorption make them very good candidates for this mode of PDT.

The conjugates of the invention are also useful for photodestruction of normal or malignant animal cells as well as of microorganisms in culture with or without SDP, enabling selective photodestruction of certain types of cells in culture or infective agents; for targeting of the porphyrin moiety to selected cells by attachment of the Chl- and Bchl-serine conjugates to specific polypeptides, such as hormones or other receptor ligands, to cell- or tissue-specific antibodies or to other ligands, e.g., lectins; for fluorescent labeling/tagging of molecules for analytical purposes in laboratory, diagnostic and industrial applications; and for fluorescent labeling of animal cells or microorganisms or particles for laboratory, diagnostic or industrial applications. They can replace several of the currently used fluorescence tags, such as fluorescein isothiocyanate (FITC) or phicoerythrine, due to their superior extinction coefficients and higher fluorescence yield.

For diagnostic purposes, the Chl and Bchl derivatives of the invention, can be radioactively-labeled by standard procedures, e.g., with $^{67}$Ga, $^{111}$In, $^{201}$Tl, $^{99}$mTc, and the radioactive diagnostic agent is administered to the patient, preferably by i.v. injection. After some hours, the locus of the cancer may be imaged by standard procedures.

The expected benefit of PDT using site-directed sensitizers is a dramatic decrease in side effects and the applied dose of sensitizer. Some particular advantages of using the proposed Chl and Bchl conjugates for PDT are as follows:

(1) These compounds have maximum optical absorption at wavelengths where the optical absorption/attenuation by human/animal tissues greatly decreases (660–830 nm in the monomeric form and up to 1000 nm in dimers or higher aggregates). Together with a decrease in light scattering, this should allow greater depth of penetration or the use of less intense and expensive light sources.

(2) Their extinction coefficients in the visible and near-IR are approximately ten times larger than those of the porphyrins currently employed for PDT.

(3) Substitution of the central Mg atom by other metals can enhance the yield of singlet oxygen production due to a higher triple state yield of the photosensitizer and can stabilize the compounds significantly.

(4) They should display increased specificity for recognition of the target cells. Therefore, lower doses of sensitizers will be sufficient for cell necrosis. In addition, the Chl and Bchl conjugates display superior photochemical properties over many presently used fluorophores and may, therefore, be practical in other applications.

(5) There are some reports indicating a high clearance rate of certain Chl derivatives from the body (Spikes and Bommer, 1991).

(6) Usually, the irradiation is carried out with laser sources such as Ar-pumped dye laser tuned to emit at 630 nm or gold-vapor laser (pulsed) that emits at 628 nm. The high cost of this equipment limits the application of PDT to larger medical centers. The use of red or near-IR absorbing photosensitizers according to the invention opens the way to more conventional and low cost means, such as Xenon flash lamps, halogen lamps, diode lasers or direct solar radiation.

(7) Radioactively or actively labeled Chl and Bchl derivatives can be used simultaneously for both diagnostic and therapeutic purposes.

The invention will now be illustrated by the following non-limitative examples.

EXAMPLES

Example 1
Preparation of Chlorophyll a

Chlorophyll a was purified from Spirullina Galtieri as follows: Lyophilized cells (2–3 g) were ground to a powder, extracted three times with acetone (10 ml), the extract was filtered and discarded. The brown-green residue was re-extracted by grinding with methanol. After filtering, the pale grey solid was discarded and the solvent was evaporated from the extract under vacuum. The green residue was redissolved in acetone and chromatographed on a column (1.5 cm diameter, 6 cm length) of diethylaminoethylsepharose (Pharmacia Fine Chemicals, DEAE-sepharose CL-6B) at 5° C. The column was washed with acetone to remove yellow materials (carotenoids), and then with methanol/acetone (1:3, v/v) to elute a dark blue solution of Chla. The total time required for the separation chromatography was 10–12 min. The Chla was checked by TLC and spectrophotometrically for residual carotenoids and other impurities such as pheophytins or chlorins, and was rechromatographed, if necessary. The methanol/acetone was then evaporated, and the solid Chla was dried thoroughly under vacuum and stored in the dark at –20° C. All operations were carried out in dim light or darkness, and were completed as rapidly as possible to minimize degradation. Analytical grade solvents were used without further purification.

Example 2
Preparation of chlorophyllase

Chlorophyllase (Chlase) acetone powder was prepared from chloroplasts of Melia azedarach L. China tree leaves. Fresh leaves (50 g) were ground with 350 ml of cold acetone (–20° C.) in a blender. The homogenate was filtered through gauze and the filtrate was left overnight at 5° C. to allow the chloroplasts sediment. The acetone was removed by filtration and the remaining powder was washed several times with 95% acetone and finally with 100% acetone, yielding chlorophyllase acetone powder which was dried under vacuum. It can be stored at –20° C. for at least several months.

Example 3
Preparation of serine derivatives

The following serine derivatives were used for thee transesterification reaction of Chla/Bchla:

(a) L-Serine methyl ester hydrochloride (L-Ser-OMe.HCl) was purchased from Sigma Chemical Co.

(b) Carbobenzoxy seryl serine methyl ester (Z-Ser$_2$-OMe): The synthesis of this new derivative was carried out using the method described by Nicolaides et al., 1968, J. Med. Chem. 11: 74–79. To a cold (5° C.) solution of 6.45 g (0.027 mole) of carbobenzoxyserine (Z-Ser) in 50 ml of DMF, 3.9 g (0.028 mole) of p-nitrophenol and 5.8 g (0.028 mole) of DCC was added. The mixture was kept at 5° C. for 5 hrs and filtered. To the filtrate, a filtered solution prepared from 4.2 g of serine methyl ester hydrochloride and 2.7 g (0.027 mole) of Et$_3$N in 50 ml of DMF was added. The reaction mixture was allowed to stand 18 hrs at 25° C., then evaporated to a small volume. The residue was taken up in 100 ml of EtOAc, and the solution, washed with H$_2$O, 5% Na$_2$CO$_3$ solution, and dilute HCl, was dried and evaporated to ca. 30 ml. Petroleum ether was added, and the resulting solid was removed and recrystallized from EtOAc-MeOH-Et$_2$O to give Z-Ser$_2$-OMe, mp 190–192° C.

(c) Carbobenzoxyserine (Z-Ser): The synthesis of this derivative, used in the synthesis of (b) above, was carried out using the method described by Moore et al., 1954, JACS 76: 2884–2887. To a cold (5° C.) solution of NaOH (212 ml, 2N), 44.3 g (0.42 mole) of L-serine was added to give pH of 9.8. At 10–15 min intervals, portions (4–5 g) of benzyl chloroformate were added and pH was adjusted to 9.8 using 1N solution of NaOH. The addition was continued until 80 g (0.46 mole) of benzyl chloroformate had been added. The pH was then maintained at 10 for 0.5 hrs at 10° C. The basic solution was extracted with 150 ml and then 100 ml of diethyl ether and 1L of EtOAc was added to the aqueous solution. By addition of 30–35 ml of concentrated HCl, the solution was acidified to pH 3 and the aqueous layer was extracted with 250 ml of EtOAc, then with 150 ml of EtOAc. The EtOAc solution was dried over $MgSO_4$ and concentrated under vacuum until Z-Ser had precipitated. Recrystallization from EtOAc gave a pure product, mp 117–119° C., total yield 79 g (78%).

(d) N-Trityl-L-serine methyl ester (Tri-Ser-OMe): The synthesis of this derivative was carried out using the method described by Guttmann, 1962, Helv. Chem. 45: 2622. To a cold (0° C.) solution of 15.5 g (0.1 mole) of L-Ser-OMe in 150 ml of chloroform, 31 ml (0.22 mole) of $Et_3N$ and 26.7 g (0.11 mole) of triphenylmethane were added. The solution was kept at 0° C. for 3 hrs, then washed with water and dried over $Na_2SO_4$. The solvent was evaporated under vacuum and a pure product 28 g (77%) was obtained, by recrystallization of the solid residue in a mixture benzene-petroleum ether (1:1).

Example 4

Preparation of L-seryl methyl ester chlorophyllidea (Chla-L-Ser-OMe) by enzymatic transesterification of Chla with L-serine methyl ester 4.1 Preparation of Chla-L-Ser-OMe 200 mg of chlorophyllase acetone powder of Example 2 was suspended in 6 ml of 0.5M sodium phosphate buffer, pH 7.6, containing 0.7% TX-100 (Triton X-100, Sigma Chem. Co.), 400 mg of L-serine methyl ester hydrochloride (Sigma) and 70 mg of ascorbic acid (Merck). The suspension was homogenized for 5 minutes and then stirred for 1 hour at room temperature. The resulting suspension was further homogenized with 5 mg of solid Chla and saturated with Ar. This mixture was sealed and incubated for 7 hours in complete darkness at 36° C., while stirring. The reaction progress was monitored by TLC on silica gel (Merck) using either n-hexane:acetone—6:4 or 1-butanol as an eluent. Three bands that corresponded to Chla, Chlidea and the title compound Chla-L-Ser-OMe were observed.

4.2 Purification of Chla-L-Ser-OMe

The reaction mixture was added to 20 ml of water containing 2 g of NaCl and 100 mg of sodium ascorbate (Sigma), and filtered under low vacuum. The blue-green residue was washed with acetone and filtered again. The filtrates were combined, saturated with NaCl and shaken with diethylether in a separatory funnel. The ethereal layer was collected and kept over solid NaCl for approximately 10 h, then evaporated in a stream of dry nitrogen and the resulting blue-green residue of the pigment was dried under vacuum. This residue was dissolved in acetone and subjected to a CM-Sepharose CL-6B column at 5° C., equilibrated with acetone. The column was washed with acetone until a brown band of pheophytines appeared, and separated from the band of the Chla-L-Ser-OMe conjugate, which remained as a blue-green band at the column top, 5% methanol/acetone and 8% methanol/acetone were used to elute the pheophorbide, respectively. Chlidea was eluted next and the Chla-L-Ser-OMe conjugate was finally eluted with 25% methanol/acetone. This last blue-green fraction was collected, checked for purity by TLC on silica gel using 1-butanol for fractionation, flushed with $N_2$ until dryness, then dried under vacuum and sealed under Ar for storage at −20° C. in the dark. Yield 75%.

4.3 Structure of the Chla-L-Ser-OMe conjugate

Figure 8A:
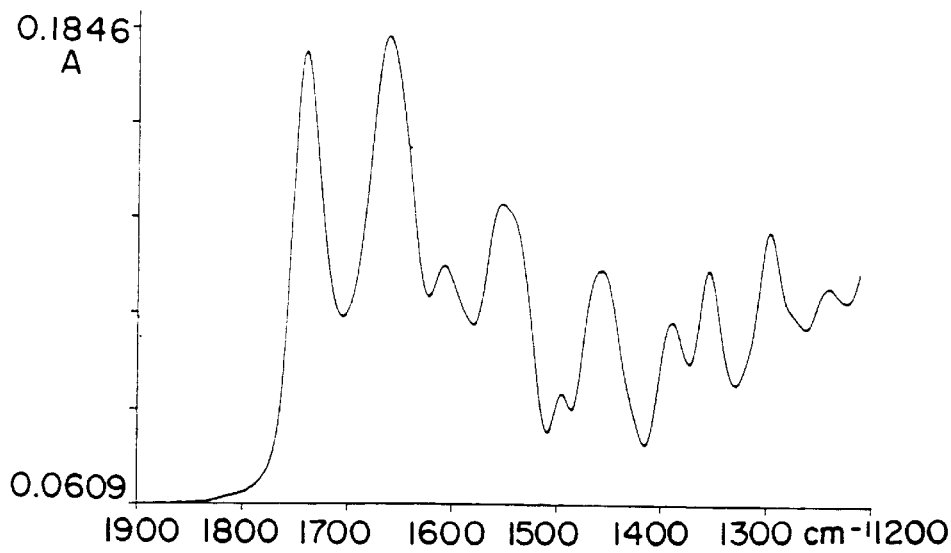
FIG. 8 shows Fourier transform infrared (FTIR) spectra of solid (a)Chla, (b)Chlidea, and (c)Chla-L-Ser-OMe.
Figure 8B:
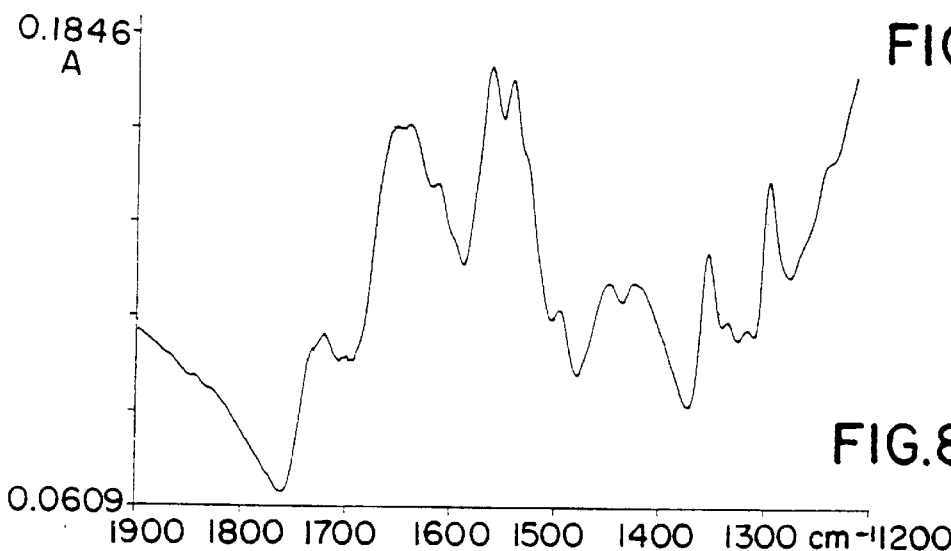
Figure 8C:
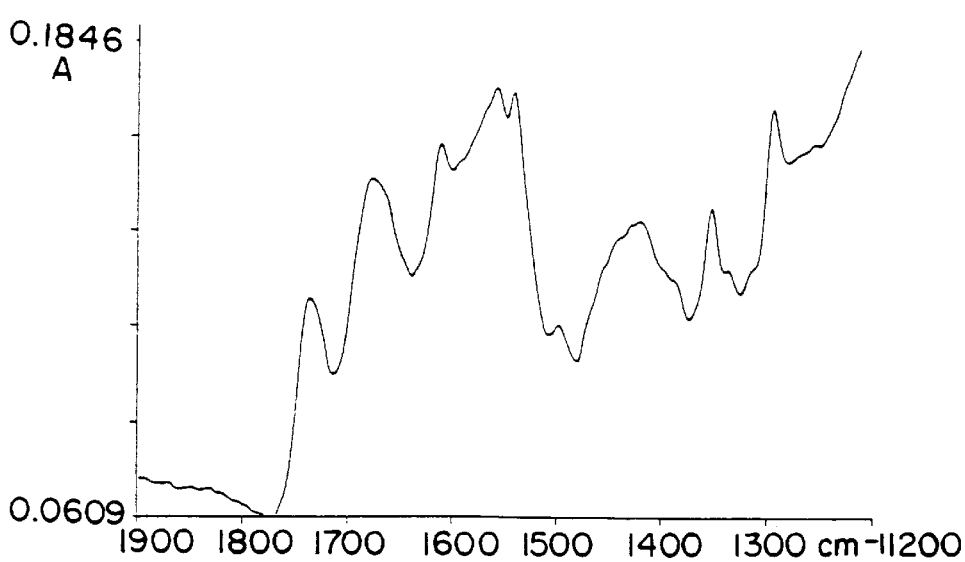

The optical absorption and FTIR spectra of Chla, Chlidea and Chla-L-Ser-OMe conjugate are shown in FIGS. 6 and 8, respectively. Each compound (within the reaction mixture) appeared as a distinct spot on a silica gel TLC. The $^1$H-NMR spectrum of the Chla-L-Ser-OMe conjugate (IV) in $CD_3OD$ as compared to the starting Chlidea (chemical shifts are listed in Table 1), has new signals at 3.57 ppm, corresponding to the serine moiety methyl group, and at 5.31–5.37 ppm, which indicate the reappearance of the ester bond. All compounds show the complete macrocycle pattern but the Chla-L-Ser-OMe conjugate IV and Chlidea miss the phytyl bands.

The FTIR spectra of Chla (a) and of the Chla-L-Ser-OMe conjugate (c) (having an ester band at 1728 cm$^{-1}$) are similar but significantly different from the spectrum of Chlidea (b), as shown in FIG. 8.

Example 5

Enzymatic transesterification of Chla with Z-Ser$_2$-OMe and Tri-Ser-OMe

The transesterification of Chla with the serine derivatives Z-Ser$_2$-OMe and Tri-Ser-OMe (compounds (b) and (d) of Example 3 above) was carried out as in Example 4 above. The TLC shows 35% yield of the Chla-serine derivatives conjugates and no hydrolysis products.

Example 6

Figure 9A:
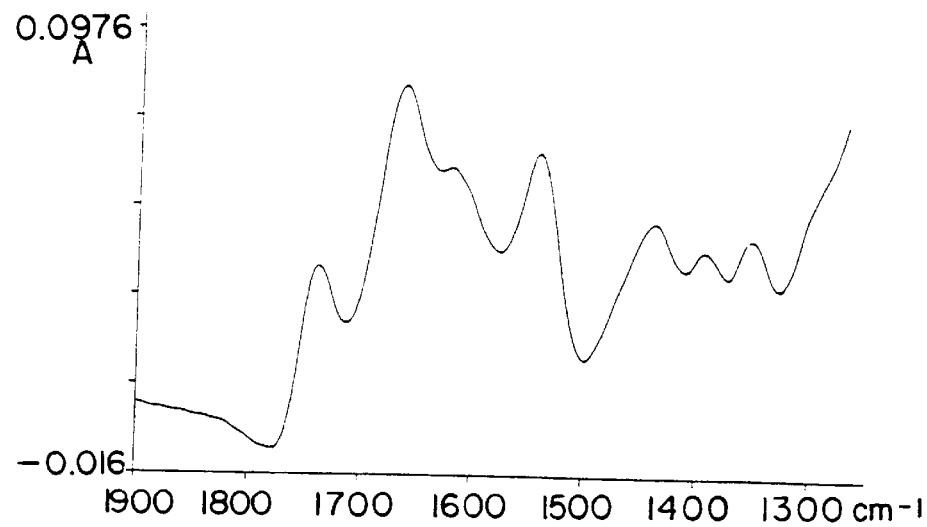
FIG. 9 shows FTIR spectra of solid (a)Bchla, (b)Bchlidea, and (c)Bchla-L-Ser-OMe.
Figure 9B:
Figure 9C:

Preparation of L-seryl methyl ester bacteriochlorophyllide a (Bchla-L-Ser-OMe) by enzymatic transesterification of Bchla with L-serine methyl ester Transesterification of Bchla with L-serine methyl ester was carried out as described in Example 4, producing Bchla-L-Ser-OMe, yield 35%. The conjugate purity was checked by TLC. Optical absorption and FTIR spectra of Bchla and Bchla-L-Ser-OMe conjugate are shown in FIGS. 6 and 9, respectively. (The chemical shifts are listed in Table 1 (compound VII)).

TABLE 1

$^1$H Chemical Shifts of Chlidea, Bchlidea and their derivatives (only high-field signals) in $CD_3OD$, in ppm

| Proton | Chlidea | Bchlidea | IV | V | VIII | IX | I | II | III |
|---|---|---|---|---|---|---|---|---|---|
| C-10 | 9.16 s | 8.60 s | 9.6 s | 9.65 s | 8.80 s | 8.80 s | — | — | — |
| C-5 | 9.48 s | 8.25 s | 9.5 s | 9.33 s | 8.42 s | 8.45 s | — | — | — |
| C-20 | 8.34 s | 8.18 s | 8.55 s | 8.45 s | 8.25 s | 8.34 s | — | — | — |
| "ester bond"* | — | — | 5.33 m | 5.10 m | 5.33 m | — | — | — | — |

TABLE 1-continued

¹H Chemical Shifts of Chlidea, Bchlidea and their derivatives (only high-field signals) in $CD_3OD$, in ppm

| Proton | Chlidea | Bchlidea | IV | V | VIII | IX | I | II | III |
|---|---|---|---|---|---|---|---|---|---|
| "amino acid residue" | — | — | — | 7.35 m | 7.35 m | 6.7–7.0 q | 7.35 m | — | 6.7–7.0 q |
| C-13[2] | 6.46 s | 6.15 s | 6.40 s | 6.70 s | 6.80 s | 6.80 s | — | — | — |

*"ester bond" between the carboxyl group of Bchlidea and Z-Ser$_2$-OMe according to FIG. 5.
I Z-Ser2-OMe — Carbobenzoxy Seryl-Serine Methyl Ester
II L-Serine — L-Serine Methyl Ester
III N-tBOC-Tyr-OMe — N-tert Butoxycarbonyl Tyrosine Methyl Ester
IV L-Seryl Methyl Ester Chlorophyllidea a
V Carbobenzoxy Seryl-Seryl Methyl Ester Chlorophyllidea a
VIII Carbobenzoxy Seryl-Seryl Methyl Ester Bacteriochlorophyllide a
IX N-tert Butoxycarbonyl Tyrosyl Methyl Ester Bacteriochlorophyllide a

Example 7

Preparation of carbobenzoxyserylseryl methyl ester chlorophyllide a by catalytic esterification of Chlidea with Z-Ser$_2$-OMe Dried Chlidea (3 mg), DCC (5.1 mg), DMAP (1.2 mg) and Z-Ser$^2$-OMe (5 fold excess) were dissolved in 1 ml of dry dichloromethane, sealed under Ar and stirred for 36 h at room temperature in the dark. The title product (V) was isolated on preparative silica gel TLC plate and then purified on DEAE-Sepharose column. The NMR spectrum of the end product is shown in Table 1. Yield 18%.

Example 8

Preparation of N-tert-Butoxycarbonyl tyrosyl methyl ester chlorophyllide a by catalytic esterification of Chlidea with N-tert-butoxycarbonyl tyrosyl methyl ester (N-tBOC-Tyr-OMe).

Dried Chlidea (3.4 mg), DCC (58 mg), DMAP (1.38 mg) and N-tBOC-Tyr-OMe (Sigma) (15 fold excess) were dissolved in 1 ml of dry dichloromethane, sealed under Ar and stirred for 40 h at room temperature in the dark. The product was isolated on preparative silica gel TLC plates and purified further on DEAE-Sepharose column. Yield 25%.

Example 9

Preparation of Bchla-serine and Bchla-tyrosine conjugates by catalytic esterification of Bchlidea with Z-Ser$_2$-OMe and N-tBOC-Tyr-OMe Esterification (condensation) of Bchlidea with each of the above compounds was carried out as described for Chlidea in examples 7–8, respectively. Table 1 shows the NMR shifts of N-tert butoxycarbonyl tyrosyl methyl ester bacteriochlorophyllide a (Bchla-N-tBOC-Tyr-OMe: compound IX) and of carbobenzoxy serylserylmethyl ester bacteriochlorophyllide a (Bchla-Z-Ser$_2$-OMe: compound VIII).

Example 10

Substitution of the central Mg in Chls and Bchls with Zn and Cu

Insertion of Zn or Cu into Chlidea-L-Ser-OMe occurs easily at room temperature under very mild conditions.

Figure 7A:
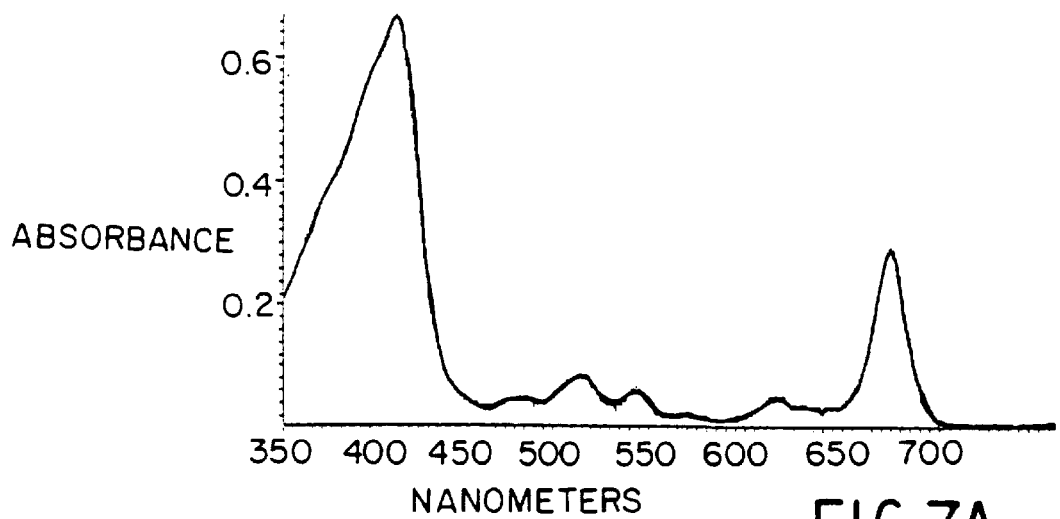
FIG. 7 shows optical absorption spectra of (a)Pheoa-L-Ser-OMe, (b)Zn-Pheoa-L-Ser-OMe, and (c)Cu-Pheoa-L-Ser-OMe, in 100% ethanol.
Figure 7B:
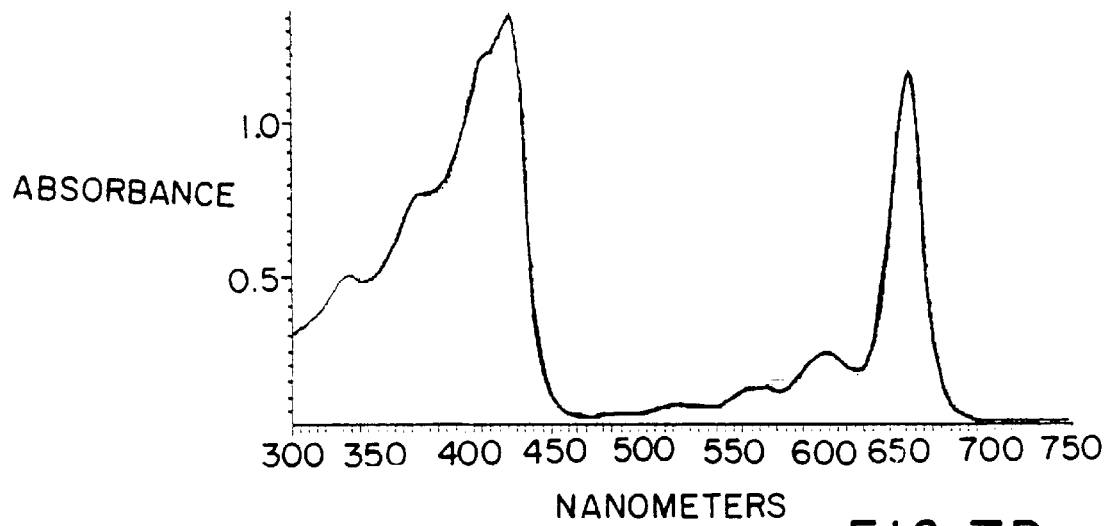
Figure 7C:
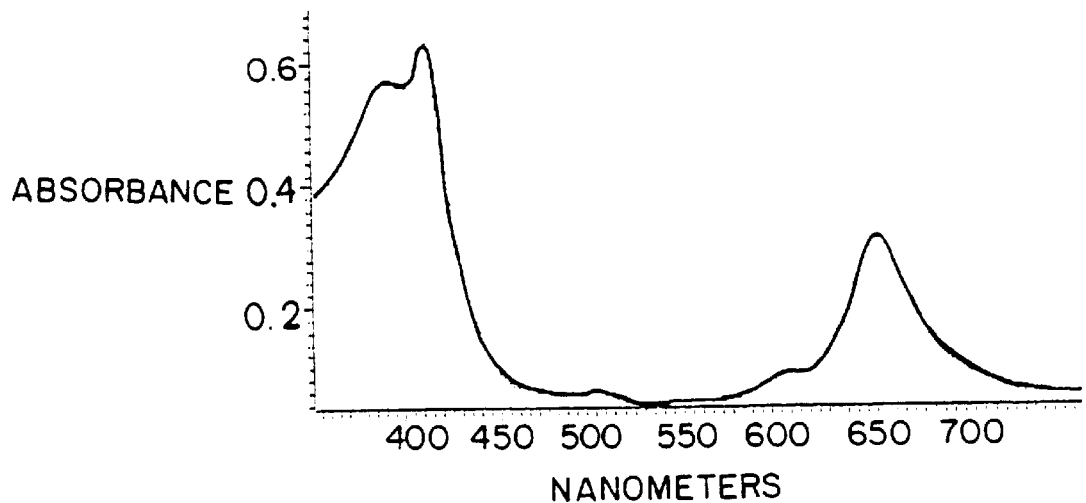

L-Seryl methyl ester pheophorbide a (Pheo-Ser-OMe—compound X) was obtained by demetalation of Chla-L-Ser-OMe in a reaction with glacial acetic acid. A small portion of Chla-L-Ser-OMe was dissolved in a few drops of acetic acid and after 10–15 seconds, the acid was evaporated under $N_2$. The brownish residue of Pheo-Ser-OMe was dissolved in 2 ml of 0.1 M solution of Zn acetate (or Cu$^{II}$ acetate) in ethanol and kept for 20 min in the dark under Ar atmosphere at room temperature while stirring. The changes in the coordination state of the macrocycle were accompanied by changes of the absorption spectra in the visible range and the reaction progress could be followed spectroscopically. Visible absorption spectra of the products are shown in FIG. 7. Under these conditions, the metalation reaction was almost quantitative and yielded pure Zn and Cu derivatives of Chla-L-Ser-OMe.

Example 11

Adsorption of Chlidea, Bchlidea and Chla and Bchla-serine conjugates to melanoma cells in culture (a) In vitro assay Monitoring the avidity of Chl and Bchl derivatives to melanoma cells was carried out as follows: M2R mouse melanoma cells (Gerst et al., 1986) were cultured as monolayers (to 100% confluence) in DMEM/F12 containing 10% horse serum at 37° C. in a humidifed atmosphere of 8% $CO_2$. 48 h later, the cells were treated with different concentrations (1–100 μM) of Chlidea, Bchlidea, Chla- and Bchla-serine conjugates and HPD (Photofrin II) for 3 h. To determine the extent of the Chl or Bchl derivative adsorption to the cells, the culture medium was aspirated, the cells were washed three times with phosphate buffered saline (PBS) and the pigments were extracted with acetone. The concentration of the Chl and Bchl derivatives in the solution was determined by comparing their optical absorption and fluorescence with those of known pigment concentrations in acetone.

Figure 10:
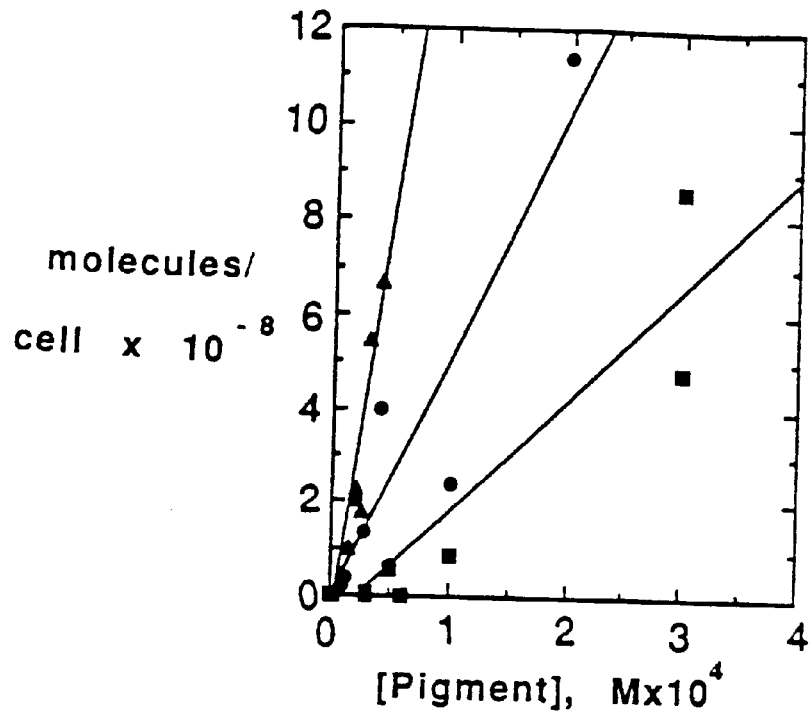
FIG. 10 depicts the dependence of Chlidea (filled triangles), Chla-L-Ser-OMe (filled circles) and HPD (filled squares) adsorption to the M2R melanoma cells in culture on the pigment concentration in the incubation medium.
Figure 11:
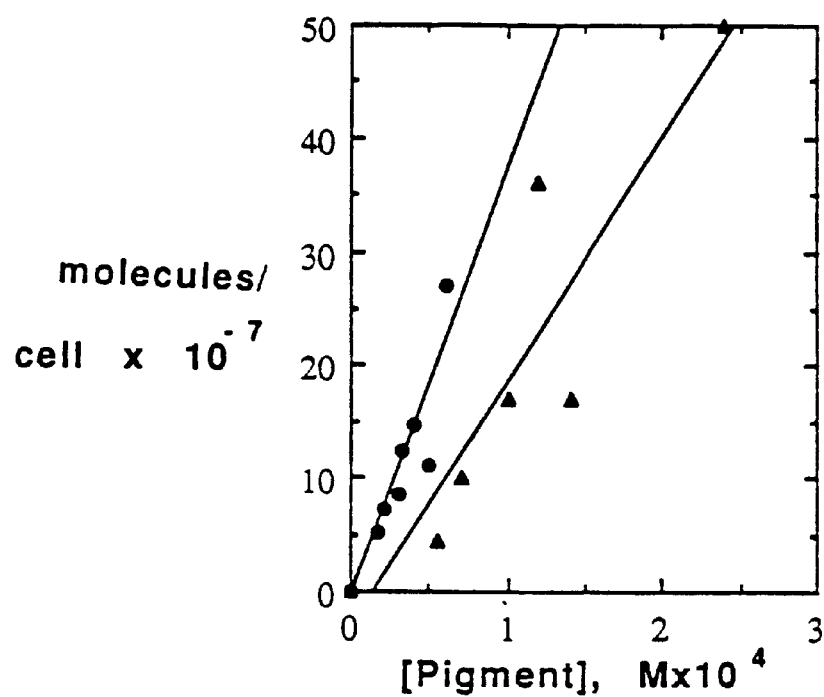
FIG. 11 depicts the dependence of Bchla-L-Ser-OMe (filled circles) and Bchlidea (filled triangles) adsorption to the M2R melanoma cells in culture as a function of the pigment concentration in the incubation medium.

The number of molecules of Chlidea and Chla-L-Ser-OMe and the corresponding Bchla derivatives adsorbed to the M2R cells following 3 h incubation in the presence of horse serum is illustrated in FIGS. 10 and 11. As can be seen, the Chlidea and Chla-L-Ser-OMe adsorb better to M2R melanoma cells than Photofrin II (HPD). Bchlidea and Bchla-L-Ser-OMe are adsorbed to melanoma cells to the same extent and about 5 times less than Photofrin II, respectively. The number of adsorbed molecules depends linearly on their initial concentration in the culture medium and the pigment adsorption reaches equilibrium during the first hour of incubation (Table 2). In the absence of serum, Chla-L-Ser-OMe adsorbed approximately 15 times better than Chla (data not shown).

TABLE 2

Cellular Adsorption
Time Dependence of Chla-L-Ser-OMe ($2.7 \times 10^{-5}$M)

| Time, h | Chla-L-Ser-OMe molecules/cell |
| --- | --- |
| 1.0 | $2.7 \times 10^7$ |
| 1.5 | $1.3 \times 10^8$ |
| 2.0 | $1.3 \times 10^8$ |

(b) In vivo assay

Chl or Bchl dissolved in 10% ethanol/PBS are injected to mice intraperitoneally (i.p.). As control groups, uninjected or vehicle injected mice are used. Sections of animal tissue or intact organs (e.g. spleen, liver, brain, etc.) are dissected, homogenized in acetone and then centrifuged. The supernatant contains the pigments. The pigment concentration in the supernatant is determined by fluorescence spectroscopy.

Example 12

Toxicity of Chl and Bchl derivatives to melanoma cells in culture

The photodynamic effect of Chlidea and Chla-L-Ser-OMe conjugate on melanoma cells in culture was tested as follows: M2R mouse melanoma cells as monolayers (to 100% confluence) were treated with the pigments Chla, Chlidea and Chla-L-Ser-OMe for 30 minutes. Subsequently the cultures were irradiated for 10 minutes from the top with a 5 mW GaAs diode laser at 670 nm (light source A), a 150 W Xenon lamp at 5000 µEinstein/cm$^2$ (light source B), or a 90 W halogen lamp at 1500 µEinstein (light source C). The control groups included untreated cells, pigment-treated cells that were kept in the dark and irradiated untreated cells. Three hours after irradiation, the changes in cell morphology due to irradiation were examined by phase contrast microscopy.

Figure 14A:
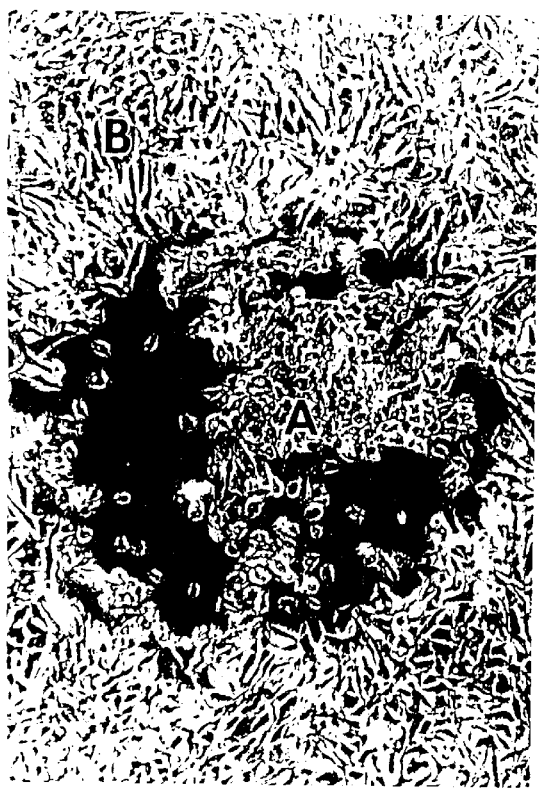
FIG. 14 shows phase contrast (left) and fluorescence (right) micrographs of an M2R cell monolayer incubated with 4×10$^{-6}$M Chla-L-Ser-OMe for 1 h and irradiated for 10 min with 670 nm laser light (5 mW). After 3 hours, the cells were treated with Propidium Iodide (PID) and their PID fluorescence was examined. A circular area irradiated by the laser beam (A) shows damaged cells and regions from which dead cells detached. Cells in the area around the irradiated zone (B) which were kept in the dark have a normal morphology (left). In the fluorescent micrograph of the same monolayer (right) all the remaining damaged cells in area (A) became PID labeled, while the cells in area (B) remained unstained and therefore are counted as unharmed.
Figure 14B:
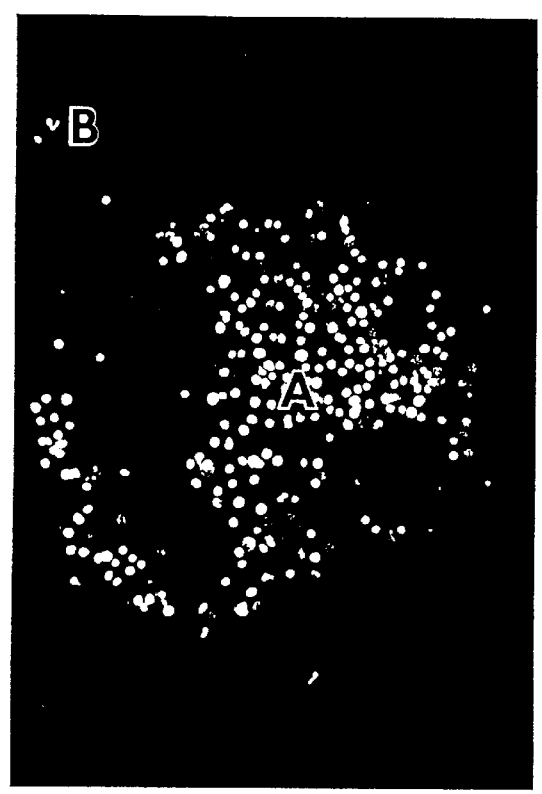
Figure 15:
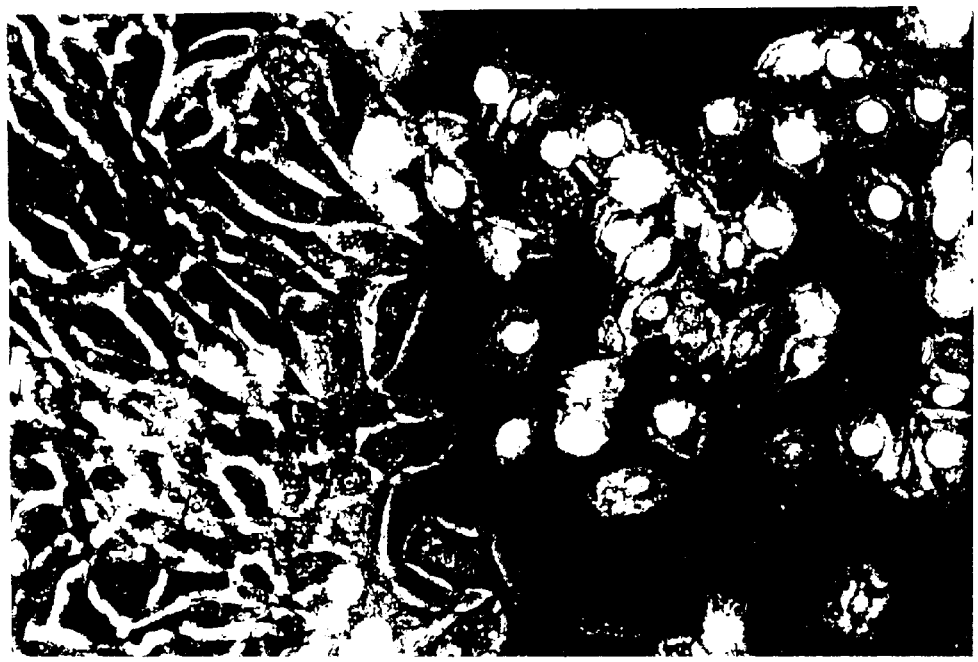
FIG. 15 shows phase contrast/fluorescence micrograph of an M2R cell monolayer treated as described in FIG. 14. Shown is the boundary of the irradiated area in which PID labeled nuclei (Nu) can be seen in damaged cells next to adjacent control cells (C) that were not irradiated and therefore have a normal morphology and unstained nuclei.

Evaluation of the cytolytic activity of the various Chl and Bchl derivatives was carried out by assessing cell death in the photodynamically treated area of the monolayer by staining of the cells with, and monitoring the red fluorescence of, Propidium Iodide ([2,7-diamino-9-phenyl-10-(diethylaminopropyl)-phenathridinium iodide meth-iodide]) (PID) which is excluded from intact/live cells and selectively accumulates in nuclei of damaged cells. Examination of fluorescing nuclei in the stained culture was done by fluorescence microscopy (Yeh, 1981). The results are shown in FIGS. 14 and 15. However, being based on microscopic examination of the treated cell cultures, this method is not the most suitable for systematic quantitative screening and evaluation of the cytolytic activity of the PDT drugs applied to a large number of cell cultures.

Alternatively, photodynamic toxicity was determined by [$^3$H] thymidine incorporation. In this case, changes in rates of [$^3$H] thymidine incorporation following PDT were performed as follows: Cell cultures (4–5×10$^4$ cells/well in about 40–50% confluency grown in 10% fetal bovine serum) were pulsed with 1µ Ci/ml thymidine [methyl-$^3$H] for 2 h at 37° C. Cultures were then washed twice with cold phosphate-buffered saline (PBS), treated with 7.5% ice cold trichloroacetic acid (TCA) for 30 min at 4° C., washed 2 times with ethanol. Cells were then dissolved in 0.3 ml of 1 M NaOH at 37° C. for 15 min. Samples of 100 µl were neutralized with 100 µl of 1N HCI and 4 ml of 0.1 M imidazole and counted in a 20:8 (vol/vol) xylene scintillator/Lumax mixture. In the experiment illustrated in FIG. 12 A, M2R cells were treated with increasing Chla-L-Ser-OMe concentrations for 60 min and subsequentlly irradiated with light source B. As can be seen the photodynamic damage is expressed by dose dependent reduction in the ability of the cells to incorporate [$^3$H] thymidine 24 h later. The effect is absolutely light dependent and was not observed in the dark controls and untreated illuminated controls. Similar results were obtained with FS11 human foreskin fibroblasts (FIG. 12B) and human T47D breast cancer cells (FIG. 12C) (using light source B). Results are given as means±SD of triplicate determiinations.

Figure 12A:
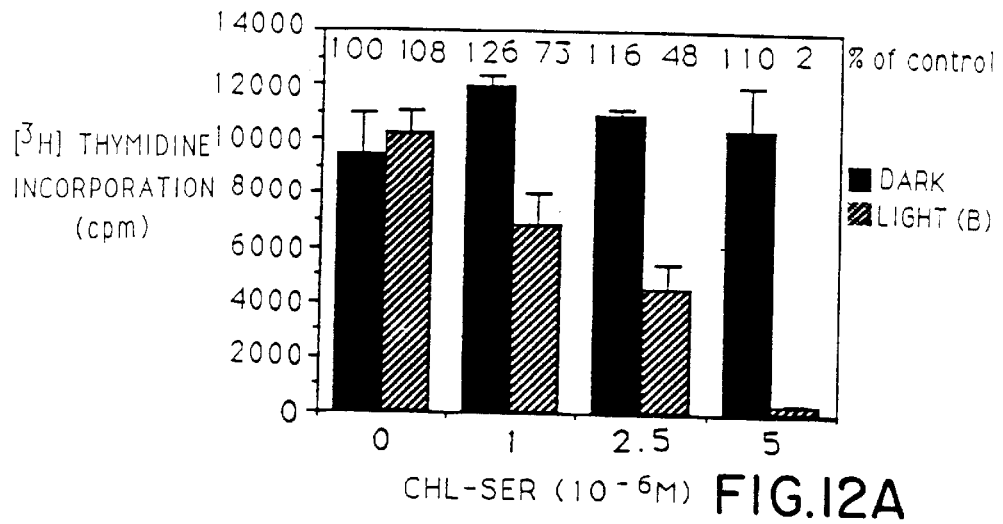
FIGS. 12 A–C show the effect of PDT on [$^3$H] thymidine incorporation in (A) M2R mouse melanoma cells, (B) FS-11 human foreskin fibroblasts and (C) T47D human breast cancer cells, upon treatment with Chla-L-Ser-OMe with (light) and without (dark) subsequent irradiation.
Figure 12B:
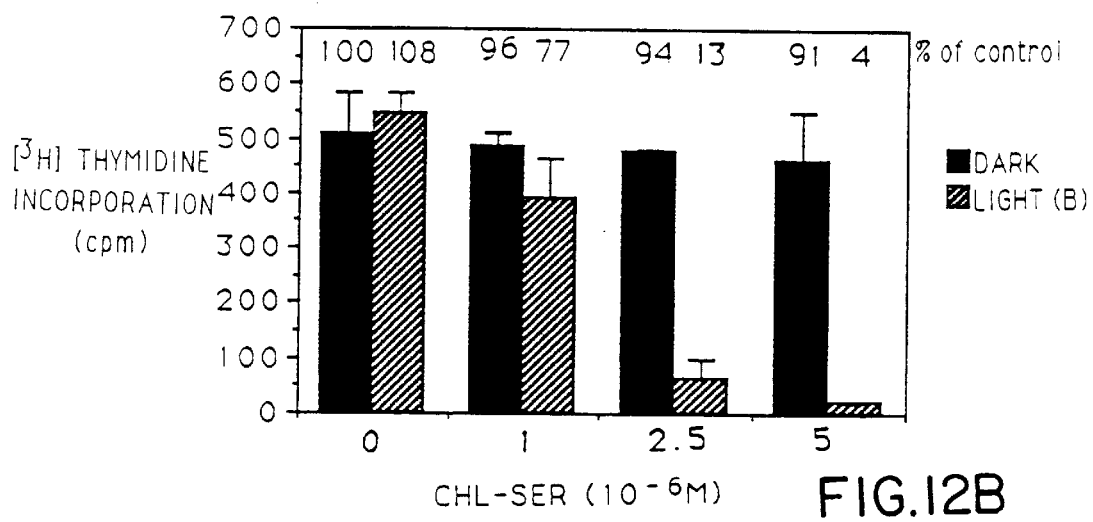
Figure 12C:
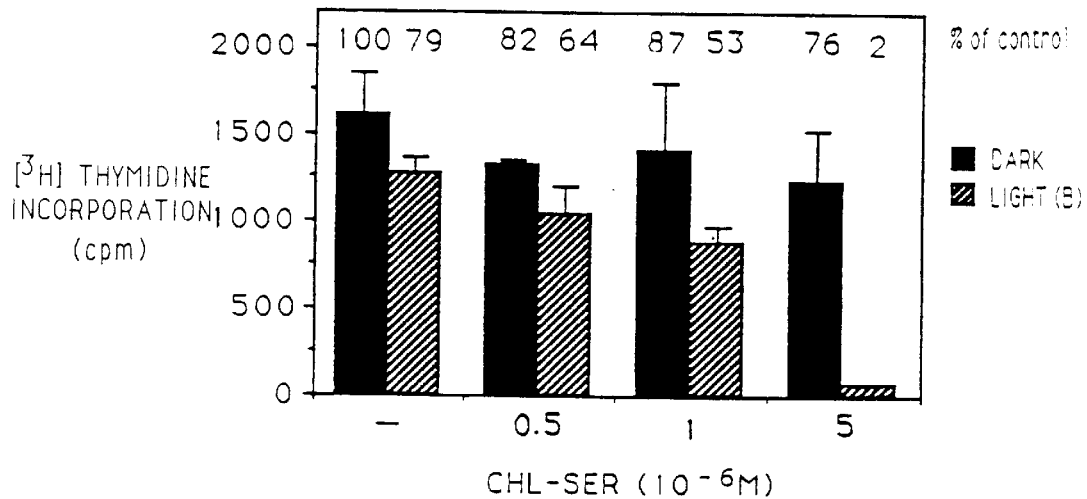

The PDT effect was also determined by the clonogenic assay: 24 h after treatment of cells with various Chla-L-Ser-Ome concentrations and completion of the irradiation step, as described above (FIG. 12A), cultures were trypsinized and viable cell numbers determined by trypan blue exclusion. Appropriate dilutions were carried out and 250 cells/well were seeded into 6-well Costar plates. After 11–12 days in culture, the medium was aspirated and the colonies were fixed and stained with crystal violet in methanol and the number of colonies (more than 40 cells per colony) was counted under a dissecting microscope. As can be seen in FIG. 13 the photodynamic treatment reduced the number of surviving cells in a dose dependent manner with respect to Chla-L-Ser-OMe, but not in the dark, or untreated illuminated controls. Comparison of the results FIGS. 12A and 13 shows a good correlation between the two methodologies. Results are given as means±SD of triplicate determinations.

Other methods that can be used in order to infer cell cytolysis include: (1) determination of cytolytic activity following [$^3$H] adenine loading of treated cells, (2) determination of cytolytic activity by $^{51}$Cr loading, and (3) detection of necrotic areas by means of video-microimaging technique. While the use of PID is based on the selective uptake of the fluorescent dye by the damaged cells only, methods 1 and 2 are based on the uptake of radioactive tracer during a preincubation step and drug induced release of radioactivity in the second step. The latter two methods are suitable for multiple assays required for detailed titrations of tens to hundreds of samples in adequate replicates.

Figure 16:
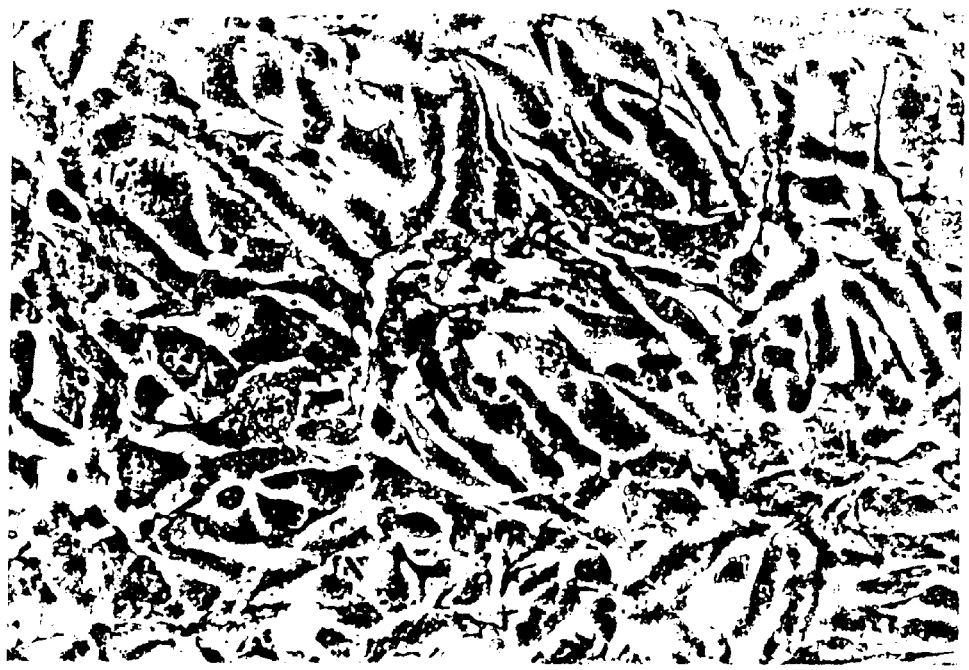
FIG. 16 shows phase contrast micrograph of an M2R cell monolayer irradiated for 10 minutes without sensitizer. No change in cell shape can be seen. No cells were labeled by PID staining (not shown).
Figure 17A:
FIG. 17 shows a cross section of skin of a photodynamically treated nude mouse (A: mag×30; B: mag×70). A nude mouse was treated with Chla-L-Ser-OMe (20 mg/Kg) and 24 h later irradiated for 4 h. Following an additional period of 24 h the mouse was sacrificed. The skin was dissected and immediately fixed in Bouin's fixative. Paraffin sections of the irradiated skin tissue were stained with modified trichrome (hematoxilin/eosin/Light green, Phosphoromolybdic acid), the orientation of the irradiated area was kept constant throughout the experiment. The section was taken through the center of the necrotic area (NC). Normal skin that was not irradiated is seen on both sides of the necrotic area (A). The necrosis penetrates the dermis and epidermis and reaches the subcutaneous fat layer which is typically loaded with fat droplets. The infiltration of leukocytes (LU) just beneath the necrotic area is also seen.
Figure 17B:

FIG. 14 shows two areas on a melanoma cell monolayer incubated for 30 minutes with $4 \times 10^{-6}$M Chla-L-Ser-OMe. Area A (FIG. 14, left) was irradiated (light source A) while area B was kept in the dark. The irradiated cells (area A) appear significantly shrunken, seem to have lost some contact with the dish and their cell membrane appears to be fragmented and irregular. PID fluorescence microscopy of the same culture (FIG. 14, right) shows that the cell damage was confined to the photodynamically treated area and that there is a 1:1 correlation between morphological changes and cell death, while nuclei of live cells did not show any fluorescence from PID (cf. areas A and B in FIG. 14, left and right). A higher magnification of the margin of the irradiated zone shows PID-treated cells with fluorescent nuclei that were irradiated and adjacent unirradiated control cells with normal morphology and unstained nuclei (FIG. 15). No damage could be identified in control untreated cells that were equally irradiated (FIG. 16). Similar changes in morphology were seen after 10 min irradiation of melanoma cells incubated with $4 \times 10^{-6}$ M Chlidea (not shown).

Example 13

Treatment of Mice with Chl and Bchl Conjugates (a) Tumor implantation: M2R cells are routinely maintained as monolayers. The cells are scraped with the aid of a rubber policeman and suspended in normal saline. 1×10$^6$ cells/0.1 ml are injected subcutaneously on the flank or batch of C57Bl or CD1 nude male mice. In approximately three–five weeks, the tumor becomes visible. These tumors grow as solid confined structures and may reach a mass of approximately 10 g, 7–8 weeks after implantation. A similar procedure is used in nude mice in which either mouse M2R or human (FO/1, MRI/H/221, HS695T amelanotic melanoma or SK/MEL/28) melanoma tumors are implanted.

(b) Injection and irradiation: Mice were injected i.p. with 20 mg/kg of the Chl and Bchl derivatives Chla-L-Ser-OMe and Bchla-L-Ser-OMe in 10% ethanol-PBS solution. After 5 hours, the tumor was irradiated for 1 hour. Control mice were (i) injected with the ethanol-PBS solution and irradiated for 1 hour; (ii) injected with the Chl and Bchl derivative and kept in the dark.

(c) 24 hours after irradiation, the mice were sacrificed by cervical dislocation. As necessary the orientation of the tumors was preserved with the aid of tissue stains and the tumors were further processed by standard histological sectioning pathways.

(d) Toxicity of the Chl and Bchl-serine conjugates Chla-L-Ser-OMe and Bchla-L-Ser-OMe in C57Bl mice under normal housing conditions in the absence of irradiation was estimated by injection of the compound dissolved in 10% ethanol/PBS. Control mice were injected with the vehicle only. It was found that injections of up to 40 mg/kg body weight had no noticeable effect on the behavior and well being of the mice for up to 14 days. This dose of drug was thus far the highest used and $LD_{50}$ vs. $EC_{50}$ of treatment (margins of therapeutic index) have yet to be determined.

(e) Skin cytotoxicity in Chla-L-Ser-OMe-treated nude mice due to focal irradiation (5 mW Ga/As diode laser 670 nm) was tested. Chl/Bchl-conjugates (20 mg/kg) in 10% ethanol/PBS were injected (i.v.) to nude mice and 24 h later the skin of the mouse was irradiated for 4 h. Control mice were (i) injected with the ethanol-PBS solution and kept in the dark; (ii) untreated and irradiated (light source A) for 4 hours. 24 hours after irradiation, the mice were sacrificed by cervical dislocation. As necessary the orientation of the irradiated zone was preserved with the aid of tissue stains and skin samples were further processed by standard histological procedures. It was found (FIG. 15) that irradiation of the skin in the experimental animal produced a lesion at the irradiated site with tissue necrosis (NC) through the dermis, epidermis and the subcutaneous fat layer (SF). A clear immune response was indicated by infiltration of leukocytes (LU) in the region directly beneath the necrotic area. The non-irradiated skin adjacent to the necrotic area appears normal. No signs of skin irritation were observed in the control group (data not shown).

(f) Photodynamic treatment of MR2 melanoma tumors with Bchla-L-Ser-OMe: 50–150 µg Bchla-L-Ser-OMe in 0.05 ml ethanol:saline 1:1 were injected under anaesthesia (Nembutal, 6.0 mg/kg) into and around the 5–6 mm diameter tumor previously implanted in a CD1 nude mouse. The injection was performed by inserting the needle through the skin 10–15 mm from the tumor and delivery of the drug into the tumor itself was done from its inner face, so that the skin above the tumor and the outer face of the tumor remained intact. The anaesthetized mouse was then placed in a bed and the site of the tumor irradiated with white halogen light at an intensity of 19000 µEinstein/cm² for 60 min. The diameter of the irradiated site was 9 mm covering only the tumor area. Follow up of the changes in tumor structure and dimension was performed over several weeks using magnetic resonance imaging (MRI). The differences in tumor shape before and after treatment are shown in FIG. 18. The tumor implanted in the upper thorax near the scapula can be clearly observed in FIG. 18A before treatment as a bright structure (T) with a high MRI signal, and was essentially eliminated 84 h later. Two weeks later, there was a small recurrence (FIG. 18B). A second treatment (Bchl-L-Ser-OMe illumination) resulted in no recurrence 3 weeks later (FIG. 18C).

(g) Retention of Chla-L-Ser-OMe in different tissues, organs and in the tumor of treated nude and black mice was assessed. Chla-L-Ser-OMe in 10% ethanol/PBS was injected to C57Bl male and CD1 male and female nude mice i.p. (20 mg/kg, average of 5–10 mice). Tissue samples (fat, muscles, skin, blood), intact organs (spleen, liver, brain, lunger, heart, etc.) and tumor were removed, homogenized in acetone and then centrifuged. The pigment concentration in the supernatant was determined by fluorescence spectroscopy. The distribution of Chla-L-Ser-OMe in the tumor and in different tissues and organs after 12 hours is shown in FIG. 19.

Example 14

Preparation of Tyrosyl Ethyl Ester Chlorophyllide and Bacteriochlorophyllide (a) Activation of Chlidea or Bchlidea with N-hydroxysuccinimide (NHS)

A mixture of vacuum-dried Chlidea or Bchlidea (5 mg) and dry NHS (9.6 mg) and DCC (5 mg) was dissolved in 2 ml of tetrahydrofuran (THF) dried over alumina. The reaction mixture was sealed under Ar and stirred for 48 hrs at room temperature and then kept for additional 48 hrs at 5° C. Each step was performed in the dark. After the reaction completion, the solvent was evaporated under $N_2$ and the green residue was redissolved in acetone and subjected to a small CM-Sepharose column (Pharmacia; 0.5×5.0 cm), equilibrated in acetone. The column was washed with 15–20 ml of acetone and the activated Chlide (NHS-Chlidea or NHS-Bchlidea) was eluted with 3–5% methanol in acetone. The eluted NHS-Chlidea or NHS-Bchlidea was further purified in the same way. Yield: 2.95–4.15 mg (50–80%).

(b) Catalytic conjugation of NHS-Chlidea and NHS-Bchlidea to tyrosine ethyl ester (Tyr-OEt)

Purified NHS-Chlidea or NHS-Bchlidea of step (a) above (2 mg) was dissolved in 1 ml of dry THF and 5 mg of tyrosine ethyl ester (Sigma) were added to the solution. The reaction mixture was sealed under Ar and stirred for 48 hrs at room temperature and then kept for 48 hrs at 5° C. in the dark. The composition of the reaction mixture was analyzed using a Vydac C-18 HPLC column (Alltech Associates, Inc., Deerfield, Ill., USA). The conditions of the separation were as follows: column—250 mm×4.6 mm; packing—Vydac 218TP, Particle size 10µ, pore size 300 Å; mobile phase—acetonitrile/water (7:3); flow rate—1 ml/min. The Chlidea-Tyr-OEt or Bchlidea-Tyr-OEt conjugate was eluted with retention time of 9.5 min. The reaction products were purified using CM-Sepharose as in example 4.

Example 15

Preparation of Chla- and Bchla-α-MSH Conjugates

α-Melanocyte stimulating hormone (MSH) has the formula:

Ser-Tyr-Ser-Met-Glu-His-Phe-Arg-Tyr-Gly-Lys-Pro-Val-NH₂

Into 1 ml of stirred solution of 1 mg of α-MSH in a 8:2 mixture of acetonitrile and water placed in a polyethylene test tube under Ar and containing 0.07 mg of triethylamine (TEA), 2.15 mg of NHS-Chlidea (prepared in Example 14a) in a small volume (about 0.2 ml) of acetonitrile was added and shortly sonicated. The reaction mixture, sealed under Ar, was stirred at room temperature in the dark for 66 hrs. In the course of the reaction, aliquots of 15 µl were taken from the reaction mixture, after 0, 3, 19, 45 and 66 hrs from the beginning of the reaction, and were subjected to HPLC analysis.

Each aliquot (15 μl) of the reaction mixture was dried under N$_2$ and redissolved in 50–100 μl of 20% acetonitrile in water containing 0.1% TFA (all v/v). The solution was injected on the C-18 HPLC column. The collected fractions had the following retention times: 24 min—unreacted α-MSH; 36 min—Chla-α-MSH conjugate; 76 min—Chlidea. The conditions of the separation were as follows: column—250 mm×4.6 mm; packing—Vydac 218TP, particle size 10μ, pore size 300 Å; mobile phase A—0.1% TFA in water; mobile phase B—0.1% TFA in acetonitrile; gradient—20% B from 0 to 5 min, then from 20 to 55% B over 10 min and from 55 to 80% B over 25 min, afterwards washing with 80% B; flow rate—1 ml/min.

The Bchla-α-MSH conjugate was prepared in a similar way but starting with Bchlidea. After purification, fractions having spectral features of a peptide and of Bchla were collected.

Figure 20:
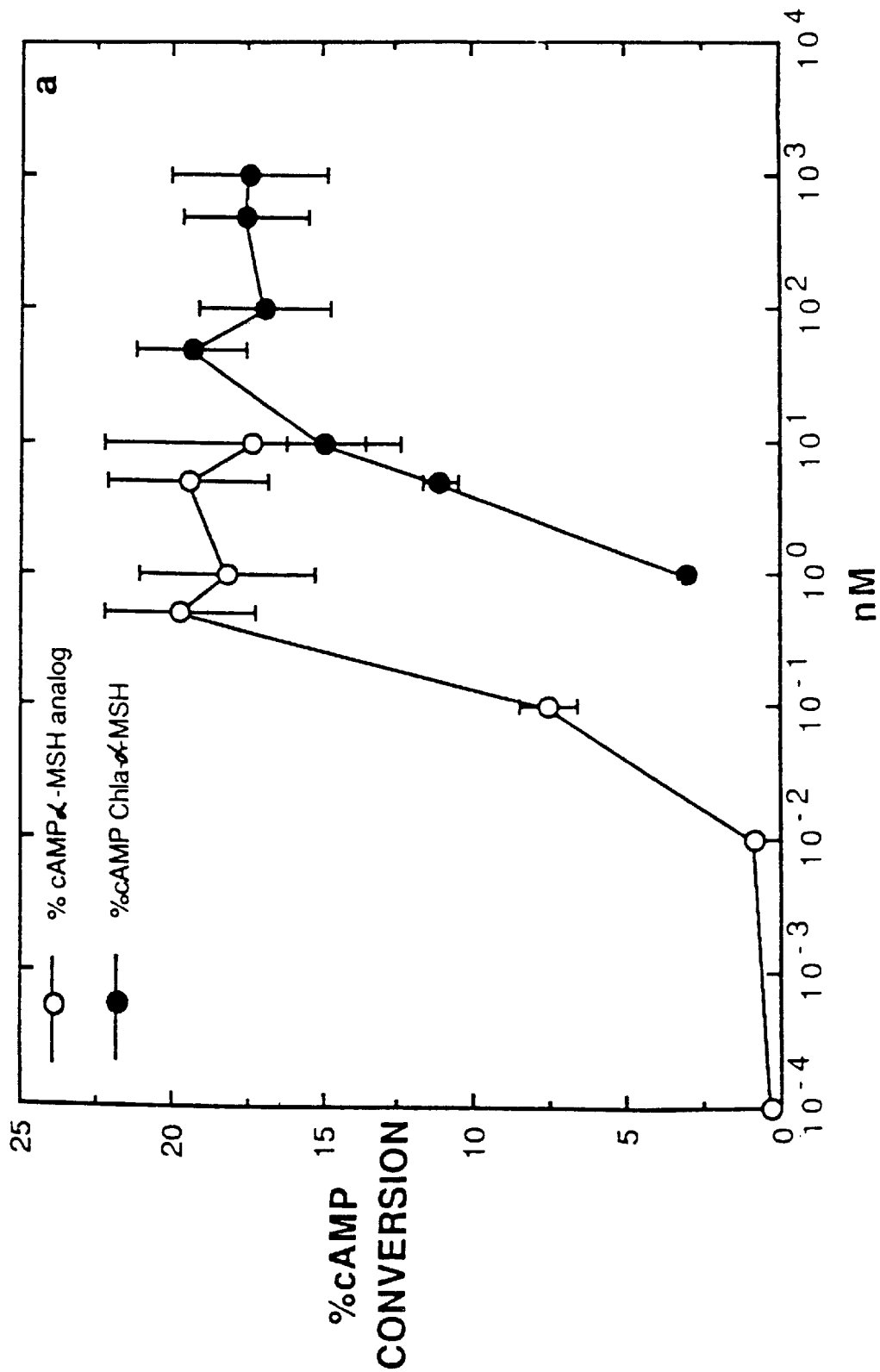
FIG. 20 shows cAMP formation in mouse MR2 melanoma cell culture, induced by Chla-α-MSH (full circles) and by an alpha-MSH analog (empty circles). The concentration of the Chla-alpha-MSH is determined by the lowest possible extinction coefficient of the Chl moiety.

The biological activity of the Chla-α-MSH conjugate was assessed by determining its ability to stimulate cyclic AMP (cAMP) in mouse M2R cell cultures as compared to [Nle$^4$, D-Phe$^7$]α-MSH, a potent α-MSH analog. cAMP accumulation was performed as described by Gerst et al, 1986. As shown in FIG. 20, the Chla-α-MSH conjugate retains identical potency when compared to the activity of the α-MSH analog.

Example 16
Preparation of Chla- and Bchla-protein Conjugates

Into 1 ml of stirred solution of a few miligrams of a protein, selected from bovine serum albumin (BSA), gamma-immunoglobulin G (IgG) and peanut agglutinin (PNA), in buffered PBS (0.1M phosphate buffer, pH=7.6) placed in a polyethylene test tube under N$_2$ and containing 0.1 mg of triethylamine (TEA), an excess of NHS-Chlidea or NHS-Bchlidea prepared in Example 14a was added over 30 min in several 10 μl portions of concentrated acetone solution, followed by a short sonication.

The amounts of the reagents in each case wre as follows:
2.5 mg of BSA—0.045 mg of NHS-Chlide
3 mg of IgG—0.041 mg of NHS-Chlide
1 mg of PNA—0.070 mg of NHS-Chlide The reaction mixture, sealed under Ar, was stirred at room temperature in the dark for 24 hrs.

The Chla- or Bchla-protein conjugate was purified on a mini-column (0.5 cm×5 cm) of Bio-Gel P-10 (Bio-Rad, Hercules, Calif., USA). The column was prepared from the gel pre-swollen in PBS, as follows: after equilibration in PBS, the column was washed with a few milliliters of BSA (1–2 mg) solution in PBS, and the excess of BSA was eluted with PBS. A small sample of the reaction mixture (50–60 μl) was loaded on the column and eluted wiyh PBS. Unreacted NHS-Chlidea or NHS-Bchlidea was retained on the top and the green band of the conjugate, which moved along the column, was collected.

The Chla- and Bchla-protein conjugates form green-coloured precipitates in aqueous solution, that can be collected upon ultracentrifugation. The precipitates can be redissolved by sonication with a detergent, e.g. 1% Triton-X 100. The conjugates show spectral features of both Chla (or Bchla) and protein. They absorb light strongly in the UV range and show bands of monomeric and aggregated Chla or Bchla (data not shown).

REFERENCES

Dougherty, T. J., Photochem. Photobiol., 1987, 45:879–889.
Fiedor, L. et al., submitted to FEBS, 1993.
Gerst, J. E., et al., Mol. and Cell. Endocrinol., 1986, 46:137–147.
Hambright, P., 1975, "Porphyrins and Metalloporphyrins", ed. Smith, K. M., Elsevier, 233–278.
Hynninen, P. A., 1991, "Chlorophylls", ed. Scheer, H. CRC Press 145–210.
Kreimer-Birnbaum, M. 1989, Seminars in Hematol. 26:157–173.
Leupold, D. and Freyer, W., J. Photochem. Photobiol. B:Biology 1992, 311–314.
Llewellyn, C. A. et al., Photochem. Photobiol., 1990 52:1043–1047.
McRobert, A. J. et al., 1989, CIBA Foundation Symposium 146, Photosensitizing compounds: Their Chemistry, Biology and Chemical Use", John Wiley & Sons, 4–12.
Moser, J. K. et al., 1992, in Abstr. Intern. Conf. PDT & Medical Laser Applications (Milan).
Spike, J. D. and Bommer, J. C., 1991 "Chlorophyll" ed. Scheer, H. CRC Press 1181–1204.
Wasielewski, M. R., Tetrahedron Let., 1977, 16:1373–1376.
Wasielewski, M. R., et al., 1980, J. Org. Chem., 45:1969.
Yeh, C.-J. G. et al., J. Immunol. Methods, 1981, 43:269–275.

We claim:

1. A process of catalytic condensation for the preparation of a compound of the formula:

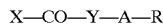

wherein
X—CO— is a C17-propionyl residue of a chlorophyll (Chl) or a bacteriochlorophyll (Bchl) or of a Chl or a Bchl in which the central Mg atom is substituted by a different divalent atom; Y is O, S or NH; A is a convalent bond or a straight or branched, saturated or unsaturated, substituted or unsubstituted C$_2$–C$_{20}$ hydrocarbon chain optionally interrupted by heteroatoms, carbocyclic or heterocyclic radicals; and R is a residue of an amino acid, peptide or protein or a derivative thereof, which comprises:
(i) reacting a chlorophyllide (Chlide) or a bacteriochlorophyllide (Bchlide) of the formula X—COOH at room temperature with an amino acid, peptide or protein or a derivative thereof of the formula R—A—OH, R—A—SH or R—A—NH$_2$ in the presence of N-hydroxysuccinimide and dicyclohexylcarbodiimide or of 4-dimethylaminopyridine and dicyclohexylcarbodiimide; and
(ii) isolating the desired compound X—CO—Y—A—R from the reaction mixture.

2. A process according to claim 1, wherein A is a covalent bond and Y is O.

3. A process according to claim 2, wherein the condensation is carried out in the presence of N-hydroxysuccinimide and dicyclohexylcarbodiimide.

4. A process according to claim 2, wherein the condensation is carried out in the presence of 4-dimethylaminopyridine and dicyclohexylcarbodiimide.

5. A process according to claim 1, for the preparation of a compound of the formula X—COOR which comprises reacting a Chlide or Bchlide of the formula X—COOH with an hydroxy-containing amino acid, peptide, protein or a derivative thereof of the formula R—OH, and isolating the desired X—COOR ester from the reaction mixture.

6. A process according to claim 5, wherein the compound R—OH is an amino acid or a derivative thereof.

7. A process according to claim 6, wherein the compound R—OH is an ester of a derivative of an amino acid.

8. A process according to claim 7, wherein the compound R—OH is N-tert butoxycarbonyltyrosyl methyl ester (N-tBOC-Tyr-OMe).

9. A process according to claim 5, wherein the compound R—OH is an ester of a peptide or of a derivative thereof.

10. A process according to claim 9, wherein the compound R—OH is carbobenzoxyserylserine methyl ester (Z-Ser$_2$-OMe).

11. A process according to claim 4 for the preparation of carbobenzoxyserylseryl methyl ester chlorophyllide (Chlide-Z-Ser$_2$-OMe) which comprises reacting Chlidea with Z-Ser$_2$-OMe in the presence of 4-dimethylaminopyridine and dicyclohexylcarbodiimide, isolating the desired Chlide-Z-Ser$_2$-OMe from the reaction mixture, and purifying it by chromatography.

12. A process according to claim 4 for the preparation of carbobenzoxyserylseryl methyl ester bacteriochlorophyllide (Bchlide-Z-Ser$_2$-OMe) which comprises reacting Bchlidea with Z-Ser$_2$-OMe in the presence of 4-dimethylaminopyridine and dicyclohexylcarbodiimide, isolating the desired Bchlide-Z-Ser$_2$-OMe from the reaction mixture, and purifying it by chromatography.

13. A process according to claim 4 for the preparation of N-tert butoxycarbonyltyrosyl methyl ester chlorophyllide (Chlide-N-tBOC-Tyr-OMe) which comprises reacting Chlide with N-tBOC-Tyr-OMe in the presence of 4-dimethylaminopyridine and dicyclohexylcarbodiimide, isolating the desired Chlide-N-tBOC-Tyr-OMe from the reaction mixture, and purifying it by chromatography.

14. A process according to claim 4, for the preparation of N-tert butoxycarbonyltyrosyl methyl ester bacteriochlorophyllide (Bchlide-N-tBOC-Tyr-OMe) which comprises reacting Bchlidea with N-tBOC-Tyr-oMe in the presence of 4-dimethylaminopyridine and dicyclohexylcarbodiimide, isolating the desired Bchlide-N-tBoc-Tyr-OMe from the reaction mixture, and purifying it by chromatography.

15. A process according to claim 3, for the preparation of a compound of the formula X—COOR, wherein the Chlide or Bchlide is first activated by reacting with N-hydroxysuccinimide (NHS) and dicyclohexylcarbodiimide, and the resulting NHS-Chlide or NHS-Bchlide is then reacted with an hydroxyl-containing amino acid, peptide or protein of the formula R—OH, the thus obtained ester X—COOR is isolated from the reaction mixture and purified by chromatography.

16. A process according to claim 15, therein R is a residue derived from an amino acid or a derivative thereof.

17. A process according to claim 16, wherein R is a residue derived from tyrosine ethyl ester.

18. A process according to claim 17, wherein R is a residue derived from a peptide or a derivative thereof.

19. A process according to claim 18, wherein R is a residue derived from a-melanocyte stimulating hormone.

* * * * *